United States Patent
Wnuk et al.

(10) Patent No.: US 10,748,056 B2
(45) Date of Patent: *Aug. 18, 2020

(54) METHODS AND SYSTEMS FOR PREDICTING DNA ACCESSIBILITY IN THE PAN-CANCER GENOME

(71) Applicants: NantOmics, LLC, Culver City, CA (US); Nant Holdings IP, LLC, Culver City, CA (US)

(72) Inventors: Kamil Wnuk, Playa del Rey, CA (US); Jeremi Sudol, Los Angeles, CA (US); Shahrooz Rabizadeh, Agoura Hills, CA (US); Patrick Soon-Shiong, Los Angeles, CA (US); Christopher Szeto, Scotts Valley, CA (US); Charles Vaske, Santa Cruz, CA (US)

(73) Assignees: NantOmics, LLC, Culver City, CA (US); Nant Holdings IP, LLC, Culver City, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/559,592

(22) Filed: Sep. 3, 2019

(65) Prior Publication Data

US 2019/0392288 A1 Dec. 26, 2019

Related U.S. Application Data

(63) Continuation of application No. 15/818,462, filed on Nov. 20, 2017, now Pat. No. 10,467,523.
(Continued)

(51) Int. Cl.
*G06N 3/04* (2006.01)
*G16B 40/00* (2019.01)
(Continued)

(52) U.S. Cl.
CPC .......... *G06N 3/04* (2013.01); *G06N 3/08* (2013.01); *G06N 7/005* (2013.01); *G16B 40/00* (2019.02); *G06N 3/0454* (2013.01)

(58) Field of Classification Search
CPC .. G06N 3/02–088; G16B 40/00; G16B 40/20; G16B 99/00
See application file for complete search history.

(56) References Cited

U.S. PATENT DOCUMENTS 10,059,989 B2   8/2018   Giresi et al.
10,467,523 B2   11/2019  Wnuk et al.
(Continued)

OTHER PUBLICATIONS

Zhou, Jiyun et al.; CNNsite: Prediction of DNA-binding Residues in Proteins Using Convolutional Neural Network with Sequence Features; 2016 IEEE International Conference on Bioinformatics and Biomedicine (BIBM); pp. 78-85. (Year: 2016).*
(Continued)

*Primary Examiner* — Stanley K. Hill
(74) *Attorney, Agent, or Firm* — Mauriel Kapouytian Woods LLP; Liang Huang; Andrew Noble

(57) ABSTRACT

Techniques are provided for predicting DNA accessibility. DNase-seq data files and RNA-seq data files for a plurality of cell types are paired by assigning DNase-seq data files to RNA-seq data files that are at least within a same biotype. A neural network is configured to be trained using batches of the paired data files, where configuring the neural network comprises configuring convolutional layers to process a first input comprising DNA sequence data from a paired data file to generate a convolved output, and fully connected layers following the convolutional layers to concatenate the convolved output with a second input comprising gene expression levels derived from RNA-seq data from the paired data file and process the concatenation to generate a DNA accessibility prediction output. The trained neural network is
(Continued)

used to predict DNA accessibility in a genomic sample input comprising RNA-seq data and whole genome sequencing for a new cell type.

32 Claims, 17 Drawing Sheets
(11 of 17 Drawing Sheet(s) Filed in Color)

Related U.S. Application Data

(60) Provisional application No. 62/540,523, filed on Aug. 2, 2017, provisional application No. 62/481,574, filed on Apr. 4, 2017, provisional application No. 62/424,370, filed on Nov. 18, 2016.

(51) Int. Cl.
  *G06N 3/08* (2006.01)
  *G06N 7/00* (2006.01)

(56) References Cited

U.S. PATENT DOCUMENTS

| 2019/0220704 A1* | 7/2019 | Schulz-Trieglaff | G06K 9/628 |
|---|---|---|---|
| 2019/0220740 A1* | 7/2019 | Xiong | G06N 3/0454 |

OTHER PUBLICATIONS

Office Action issued in Australian Application No. 2017362569 dated Jan. 8, 2020, 2 pages.
Abadi et al., "TensorFlow: Large-scale machine learning on heterogeneous systems," arXiv preprint arXiv:1603.04467, 2015, 19 pages.
Alipanahi et al., "Predicting the sequence specificities of DNA- and RNA-binding proteins by deep learning," Nature Biotechnology, 2015, vol. 33, No. 8, pp. 831-838.
Angermueller et al., "DeepCpG: accurate prediction of single-cell DNA methylation states using deep learning," Genome Biology, 2017, vol. 18, 13 pages.
Bahdanau et al., "Neural machine translation by jointly learning to align and translate," arXiv preprint arXiv:1409.0473, 2014, 15 pages.
Breschi et al., "Gene-specific patterns of expression variation across organs and species," Genome Biology, 2016, vol. 17, No. 1, 13 pages.
Conesa et al., "A survey of best practices for RNA-seq data analysis," Genome Biology, 2016, vol. 17, No. 1, 19 pages.
ENCODE Project Consortium, "An integrated encyclopedia of DNA elements in the human genome," Nature, 2012, vol. 489, No. 7414, pp. 57-74.
Deplancke et al., "The genetics of transcription factor DNA binding variation," Cell, 2016, vol. 166, No. 3, pp. 538-554.
GTEx Consortium, "The genotype-tissue expression (GTEx) project," Nature Genetics, 2013, vol. 45, No. 6, pp. 580-585.
He et al., "Deep residual learning for image recognition," In Proceedings of the IEEE Conference on Computer Vision and Pattern Recognition, 2016, pp. 770-778.
Hochreiter et al., "Long short-term memory," Neural Computation, 1997, vol. 9, No. 8, pp. 1735-1780.
Kelley et al., "Basset: learning the regulatory code of the accessible genome with deep convolutional neural networks," Genome Research, 2016, vol. 26, pp. 990-999.
Kingma et al., "Adam: A method for stochastic optimization," arXiv preprint arXiv:1412.6980, 2014, 15 pages.
Lanchantin et al., "Deep motif: Visualizing genomic sequence classifications," arXiv preprint arXiv:1605.01133, 2016, 5 pages.
Maurano et al., "Systematic localization of common disease-associated variation in regulatory DNA," Science, 2012, vol. 337, Issue 6099, pp. 1190-1195.
Kundaje et al., "Integrative analysis of 111 reference human epigenomes," Nature, 2015, vol. 518, No. 7539, pp. 317-330.
Sheffield et al., "Patterns of regulatory activity across diverse human cell types predict tissue identity, transcription factor binding, and long-range interactions," Genome Research, 2013, vol. 23, Issue 5, pp. 777-788.
Simonyan et al., "Very deep convolutional networks for large-scale image recognition," ICLR, 2015, 14 pages.
Singh et al., "Predicting enhancer-promoter interaction from genomic sequence with deep neural networks," bioRxiv, 2016, 12 pages.
Sudmant et al., "Meta-analysis of RNA-seq expression data across species, tissues and studies," Genome Biology, 2015, vol. 16, No. 1, 11 pages.
Szegedy et al., "Rethinking the inception architecture for computer vision," 2016 IEEE Conference on Computer Vision and Pattern Recognition (CVPR), pp. 2818-2826.
Xu et al., "Show, attend and tell: Neural image caption generation with visual attention," In International Conference on Machine Learning, 2015, 10 pages.
Van Der Maaten et al., "Visualizing data using t-sne," Journal of Machine Learning Research, 2008, vol. 9, pp. 2579-2605.
Vaske et al., "Inference of patient-specific pathway activities from multi-dimensional cancer genomics data using PARADIGM," Bioinformatics, 2010, vol. 26, No. 12, pp. i237-i245.
Voss et al., "Dynamic regulation of transcriptional states by chromatin and transcription factors," Nature Reviews Genetics, 2014 vol. 15, No. 2, pp. 69-81.
International Search Report and Written Opinion issued in International Application No. PCT/US2017/062626 dated Feb. 19, 2018, 15 pages.
Hashimoto et al., "A synergistic DNA logic predicts genome-wide chromatin accessibility," Genome Research, 2016, vol. 26, No. 10, pp. 1430-1440.
Natarajan et al., "Predicting cell-type—specific gene expression from regions of open chromatin," Genome Research, 2012, vol. 22, pp. 1711-1722.
Quang et al., "DanQ: a hybrid convolutional and recurrent deep neural network for quantifying the function of DNA sequences," Nucleic Acids Research, 2016, vol. 44, No. 11, 6 pages.
Wnuk et al., "Predicting DNA accessibility in the pan-cancer tumor genome using RNA-seq, WGS, and deep learning," bioRxiv, 2017, 16 pages.
Harrow et al., "GENCODE: The reference human genome annotation for The ENCODE Project," Genome Research, 2012, vol. 22, No. 9, pp. 1760-1774.
Zerbino et al., "The Ensembl Regulatory Build," Genome Biology, 2015, vol. 16, No. 1, 8 pages.
Zhou et al., "Predicting effects of noncoding variants with deep learning—based sequence model," Nature Methods, 2015, vol. 12, No. 10, 15 pages.
International Preliminary Report on Patentability issued in International Application No. PCT/US2017/062626 dated May 31, 2019, 11 pages.
Huang et al., "Densely connected convolutional networks," arXiv preprint arXiv:1608.06993, 2016, 9 pages.
Kundaje, "DAC Blacklisted Regions," https://www.encodeproject.org/annotations/ENCSR636HFF/, 1 page, 2018.
Library of Integrated Network-based Cellular Signatures (LINCS), L1000 genes, GEO accession GPL20573, https://www.ncbi.nlm.nih.gov/geo/query/acc.cgi?acc=GPL20573, 2 pages, 2015.
TCGA Research Network, "The cancer genome atlas," http://cancergenome.nih.gov/, 2018.
Office Action issued in Korean Application No. 10-2019-7016912 dated Jun. 18, 2020, 12 pages.
Blatti et al., "Integrating motif, DNA accessibility and gene expression data to build regulatory maps in an organism," Nucleic Acids Research, vol. 43, No. 8, 2015, pp. 3998-4012.

* cited by examiner

METHODS AND SYSTEMS FOR PREDICTING DNA ACCESSIBILITY IN THE PAN-CANCER GENOME

CROSS REFERENCE TO RELATED APPLICATIONS

This application is a continuation application of U.S. application Ser. No. 15/818,462 filed on Nov. 20, 2017, which claims priority to U.S. Provisional Application No. 62/540,523 filed on Aug. 2, 2017 and claims priority to U.S. Provisional Application No. 62/481,574 filed on Apr. 4, 2017 and claims priority to U.S. Provisional Application No. 62/424,370 filed on Nov. 18, 2016. The entire contents of these applications are hereby incorporated herein by reference.

TECHNICAL FIELD

This disclosure relates generally to predicting DNA accessibility in a genomic sample, and more specifically to using a neural network to predict DNA accessibility in a genomic sample.

BACKGROUND

DNA accessibility, along with chromatin regulation and genome methylation, plays a key role in the regulatory machinery of DNA transcriptional events that can promote tumor growth. Locations where DNA is not tightly bound in nucleosomes, detectable as DNase I hypersensitivity (DHS) sites, can render a DNA sequence accessible to other DNA-binding proteins, including a wide range of transcription factors (TFs). DHS sites are cell specific and play a crucial role in determining cell-selective transcriptional events.

Furthermore, genome wide association studies (GWAS) have revealed that the vast majority of genetic variants significantly associated with many diseases and traits are located in non-coding regions. Among such non-coding single nucleotide polymorphisms (SNPs), well over half affect DHS sites. Thus, variable access to DNA regulatory elements not only plays a key role in normal cell development, but also in altered expression profiles associated with disease states.

However, understanding the impact of DNA sequence data on transcriptional regulation of gene expression is a challenge, particularly in noncoding regions of the genome.

In an effort go beyond genome wide association studies and gain deeper insight into how changes in DNA sequence data impact transcriptional regulation, neural network models have been developed for predicting DNA accessibility in multiple cell types. In theory, these models can make it possible to explore the impact of mutations on DNA accessibility and transcriptional regulation.

One common issue that limits the broad applicability of neural networks for predicting DNA accessibility is the cell-type-specific nature of many of the underlying biological mechanisms, such as DHS sites. Current examples of neural network models have addressed this issue by either training a separate model for each cell type or by having a single model output multiple cell-type-specific (multi-task) predictions. However, these limitations make it difficult to apply current neural network models to new data and limits them from being integrated into broader scope pathway models. Thus, there remains a need for a neural network solution that overcomes the current barrier to broad applicability due to cell-specific phenomena.

SUMMARY

Systems, methods, and articles of manufacture related to using a neural network to predict DNA accessibility in a genomic sample are described herein. The various embodiments are based on the utility of RNA-seq data as a signal for cell type clustering and classification. Given paired RNA-seq and DNase-seq input data, a neural network is configured to learn to appropriately modulate its prediction to eliminate the need for a distinct trained model or unique output per cell type. As such, for the first time, accurate DNA accessibility predictions can be made for previously unseen cell types whose gene expressions are similar but unique from samples in the training data.

In one embodiment, genomic sample data including DNase-seq data files and RNA-seq data files for a plurality of cell types is obtained. Paired data files are generated from the genomic sample data by assigning DNase-seq data files to RNA-seq data files that are at least within a same biotype. A neural network is configured to be trained to predict DNA accessibility based on RNA-seq data using a plurality of batches of the paired data files, where configuring the neural network comprises configuring convolutional layers of the neural network to process a first input comprising DNA sequence data from one of the paired data files to generate a convolved output, and fully connected layers of the neural network following the convolutional layers to concatenate the convolved output with a second input comprising gene expression levels derived from RNA-seq data from the one of the paired data files and process the concatenation to generate a DNA accessibility prediction output. The first input may comprise a 600-base pair segment of DNA, and the gene expression levels may correspond to a selected subset of genes. The DNA accessibility prediction output may be a single prediction. The neural network is trained using the plurality of batches of the paired data files, and a computing device is configured to use the trained neural network to predict DNA accessibility in a genomic sample input comprising RNA-seq data and whole genome sequencing for a new cell type with respect to the genomic sample data. The genomic sample input may be associated with a cancer cohort from The Cancer Genome Atlas (TCGA) or a tumor.

In some embodiments, the genomic sample data may be obtained from at least one of ENCODE project data and Roadmap Epigenomics project data. The RNA-seq data files may include data files having one or more of RNA-seq, polyA mRNA, polyA depleted, and single cell ENCODE labels, and RNA-seq data files that include error audit flags from the genomic sample data may be removed. The paired data files may be generated by assigning DNase-seq data files to RNA-seq data files based on matching biosample accessions or being from at least one of a same tissue sample, same cell line, or same patient. The paired data files may also be generated by randomly assigning a DNase-seq data file to one of a plurality of RNA-seq data files determined to be within a same biotype.

In some embodiments, the neural network may comprise a hierarchical structure of a plurality of convolutional layers each succeeded by a max-pooling layer, and the hierarchical structure may comprise at least three convolutional layers. The neural network may further comprise at least two fully connected layers following the hierarchical structure.

In some embodiments, training the neural network may comprise increasing a dynamic decay rate over a course of training when moving averages are updated for batch normalization, and using an adaptive moment estimation (Adam) optimization algorithm to optimize one or more network parameters of the neural network.

In some embodiments, the neural network may comprise a deep convolutional neural network, or a densely connected convolutional neural network.

In one embodiment, a convolutional neural network system comprises a sequence of neural network layers comprising a hierarchical structure of a plurality of convolutional layers each succeeded by a max-pooling layer. The hierarchical structure is configured to receive a first input comprising DNA sequence data from a paired data file and process the first input to generate a convolved output. The paired data file is generated from genomic sample data for a plurality of cell types by assigning DNase-seq data files to RNA-seq data files that are at least within a same biotype. The hierarchical structure may comprise at least three convolutional layers. At least two fully connected layers follow the hierarchical structure, and the at least two fully connected layers are configured to concatenate the convolved output with a second input comprising gene expression levels derived from RNA-seq data from the paired data file and process the concatenation to generate a DNA accessibility prediction output, that may be a single prediction. The sequence of neural network layers may be trained to predict DNA accessibility based on RNA-seq data using a plurality of batches of paired data files. A dynamic decay rate for the sequence of neural network layers may be configured to be increased over a course of training when moving averages are updated for batch normalization, and one or more network parameters of the sequence of neural network layers may be configured to be optimized based on an adaptive moment estimation (Adam) optimization algorithm.

In some embodiments, the sequence of neural network layers may comprise a deep convolutional neural network or a densely connected convolutional neural network.

Various objects, features, aspects and advantages of the inventive subject matter will become more apparent from the following specification, along with the accompanying drawings in which like numerals represent like components.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 1:
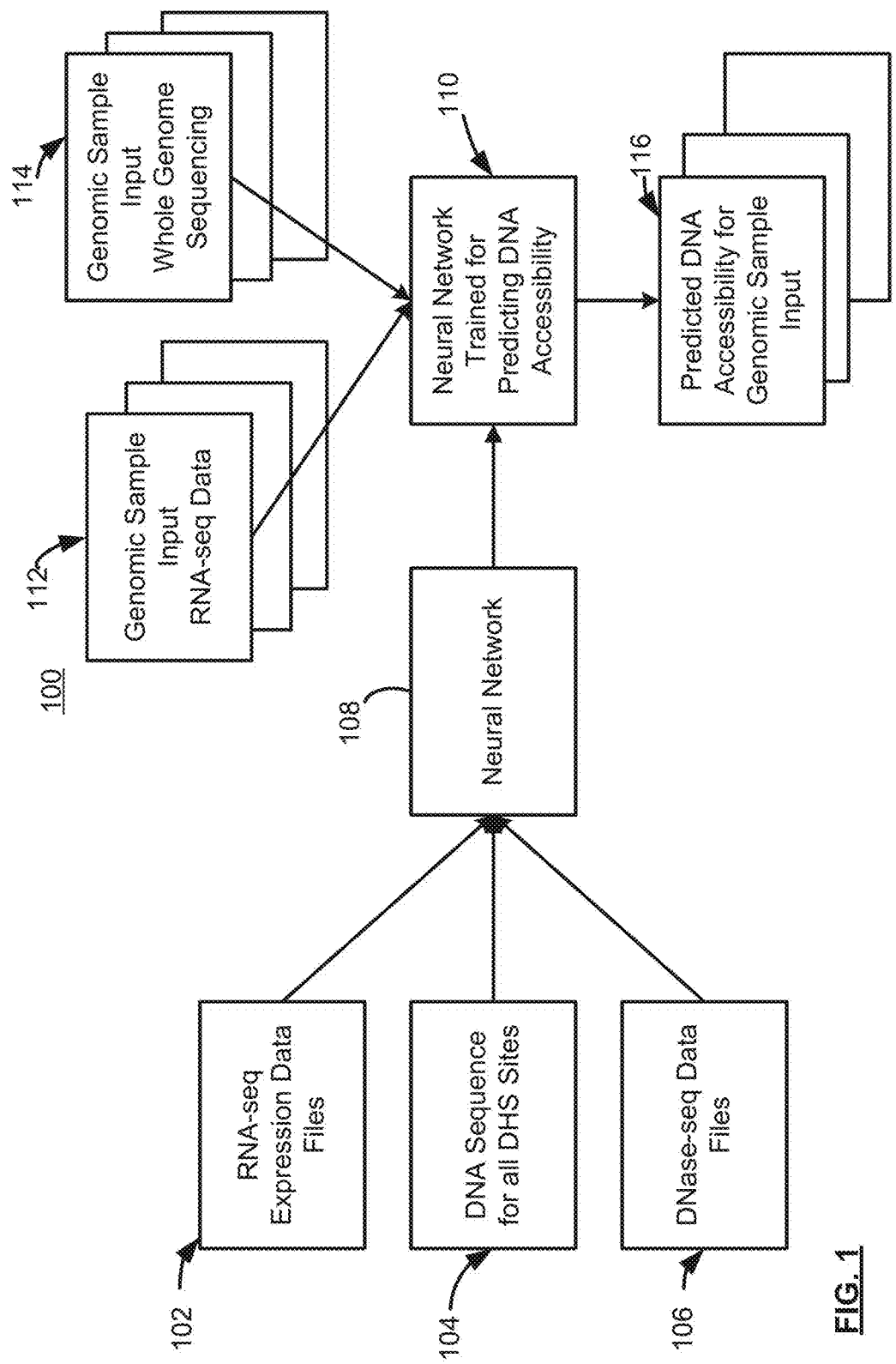
FIG. 1 illustrates an overview flow diagram of example operations for predicting DNA accessibility using RNA-seq data in accordance with an embodiment.

While the invention is described with reference to the above drawings, the drawings are intended to be illustrative, and other embodiments are consistent with the spirit, and within the scope, of the invention.

SPECIFICATION

The various embodiments now will be described more fully hereinafter with reference to the accompanying drawings, which form a part hereof, and which show, by way of illustration, specific examples of practicing the embodiments. This specification may, however, be embodied in many different forms and should not be construed as being limited to the embodiments set forth herein; rather, these embodiments are provided so that this specification will be thorough and complete, and will fully convey the scope of the invention to those skilled in the art. Among other things, this specification may be embodied as methods or devices. Accordingly, any of the various embodiments herein may take the form of an entirely hardware embodiment, an entirely software embodiment or an embodiment combining software and hardware aspects. The following specification is, therefore, not to be taken in a limiting sense.

Throughout the specification and claims, the following terms take the meanings explicitly associated herein, unless the context clearly dictates otherwise:

The phrase "in one embodiment" as used herein does not necessarily refer to the same embodiment, though it may. Thus, as described below, various embodiments of the invention may be readily combined, without departing from the scope or spirit of the invention.

As used herein, the term "or" is an inclusive "or" operator, and is equivalent to the term "and/or," unless the context clearly dictates otherwise.

The term "based on" is not exclusive and allows for being based on additional factors not described, unless the context clearly dictates otherwise.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously. Within the context of a networked environment where two or more components or devices are able to exchange data, the terms "coupled to" and "coupled with" are also used to mean "communicatively coupled with", possibly via one or more intermediary devices.

In addition, throughout the specification, the meaning of "a", "an", and "the" includes plural references, and the meaning of "in" includes "in" and "on".

Although some of the various embodiments presented herein constitute a single combination of inventive elements, it should be appreciated that the inventive subject matter is considered to include all possible combinations of the disclosed elements. As such, if one embodiment comprises elements A, B, and C, and another embodiment comprises elements B and D, then the inventive subject matter is also considered to include other remaining combinations of A, B, C, or D, even if not explicitly discussed herein. Further, the transitional term "comprising" means to have as parts or members, or to be those parts or members. As used herein, the transitional term "comprising" is inclusive or open-ended and does not exclude additional, unrecited elements or method steps.

Throughout the following discussion, numerous references will be made regarding servers, services, interfaces, engines, modules, clients, peers, portals, platforms, or other systems formed from computing devices. It should be appreciated that the use of such terms is deemed to represent one or more computing devices having at least one processor (e.g., ASIC, FPGA, DSP, x86, ARM, ColdFire, GPU, multi-core processors, etc.) configured to execute software instructions stored on a computer readable tangible, non-transitory medium (e.g., hard drive, solid state drive, RAM, flash, ROM, etc.). For example, a server can include one or more computers operating as a web server, database server, or other type of computer server in a manner to fulfill described roles, responsibilities, or functions. One should further appreciate the disclosed computer-based algorithms, processes, methods, or other types of instruction sets can be embodied as a computer program product comprising a non-transitory, tangible computer readable medium storing the instructions that cause a processor to execute the disclosed steps. The various servers, systems, databases, or interfaces can exchange data using standardized protocols or algorithms, possibly based on HTTP, HTTPS, AES, public-private key exchanges, web service APIs, known financial transaction protocols, or other electronic information exchanging methods. Data exchanges can be conducted over a packet-switched network, a circuit-switched network, the Internet, LAN, WAN, VPN, or other type of network.

As used in the description herein and throughout the claims that follow, when a system, engine, server, device, module, or other computing element is described as configured to perform or execute functions on data in a memory, the meaning of "configured to" or "programmed to" is defined as one or more processors or cores of the computing element being programmed by a set of software instructions stored in the memory of the computing element to execute the set of functions on target data or data objects stored in the memory.

It should be noted that any language directed to a computer should be read to include any suitable combination of computing devices, including servers, interfaces, systems, databases, agents, peers, engines, controllers, modules, or other types of computing devices operating individually or collectively. One should appreciate the computing devices comprise a processor configured to execute software instructions stored on a tangible, non-transitory computer readable storage medium (e.g., hard drive, FPGA, PLA, solid state drive, RAM, flash, ROM, etc.). The software instructions configure or program the computing device to provide the roles, responsibilities, or other functionality as discussed below with respect to the disclosed apparatus. Further, the disclosed technologies can be embodied as a computer program product that includes a non-transitory computer readable medium storing the software instructions that causes a processor to execute the disclosed steps associated with implementations of computer-based algorithms, processes, methods, or other instructions. In some embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges among devices can be conducted over a packet-switched network, the Internet, LAN, WAN, VPN, or other type of packet switched network; a circuit switched network; cell switched network; or other type of network.

The focus of the disclosed inventive subject matter is to enable construction or configuration of a computing device to operate on vast quantities of digital data, beyond the capabilities of a human for purposes including predicting DNA accessibility in a genomic sample.

One should appreciate that the disclosed techniques provide many advantageous technical effects including improving the scope, accuracy, compactness, efficiency and speed of predicting DNA accessibility in a genomic sample using a neural network. It should also be appreciated that the following specification is not intended as an extensive overview, and as such, concepts may be simplified in the interests of clarity and brevity.

Predicting DNA Accessibility Using RNA-Seq Data

In cell-type specific DNA accessibility neural network models, each new type of genomic sample (e.g., a biological cell or tissue for a given biotype) encountered requires the neural network to first be trained with DNase I hypersensitive site sequencing (DNase-seq) peaks measured from the new type of genomic sample before any DNA accessibility predictions can be made. The Basset neural network model is one example of a cell-type specific model for predicting DNA accessibility. The Basset neural network model uses a binary matrix of genomic sample types and their respective DNA accessibilities as a universal list of potentially accessible genomic sites. Before training the Basset neural network model, the universal list is generated by agglomeratively clustering all overlapping DNase-seq peaks across all genomic samples. The final layer of the Basset neural network model is a multi-task output with a distinct prediction unit (output) for each biotype.

However, this limitation of cell-type specific DNA accessibility prediction models (i.e., the discretization of cell types) can be avoided by using a supplementary numerical signature that characterizes cells and tissues. Having such a cell signature as a parallel input can enable a neural network to leverage similarity and structure in the space of cell types and learn how DNA accessibility is modulated in a more general way (i.e., by a genomic sample's coordinates in the cell signature space).

It has been determined that one candidate for such a supplementary signature is RNA-sequencing (RNA-seq) data, i.e., the presence and quantity of RNA in a biological sample at a given moment in time, which is commonly available across large data sources of interest in research such as, for example, TCGA and the Genotype-Tissue Expression (GTEx) project. Several studies indicate that gene expression levels estimated or derived from RNA-seq data can be used as a supplementary signature input into a neural network for predicting DNA accessibility. For example, DNase-seq and microarray based gene expression levels from matched samples have been found to cluster similarly according to biological relationships, and many DNase I hypersensitivity (DHS) sites have been found to significantly correlate with gene expressions. Similar biologically meaningful neighborhood relationships also have appeared in both DNase-seq and RNA-seq data collected from the ENCODE project. Moreover, it has been observed that DNA accessibility is one of many complex factors that eventually determine gene expression at the level of RNA-seq, which makes the relationship between DNA accessibility and RNA-seq data not trivially invertible. While the knowledge of gene expression levels does not uniquely define the pattern of DHS sites, a most likely mechanism with which the DNA sequence immediately surrounding a potential DHS site determines its accessibility can be learned in the context of observed gene expression levels. Thus, when a DNA accessibility prediction determined using RNA-seq data is applied across the whole genome, it can be viewed as an approach that inverts gene expression to obtain most likely DHS sites, constrained only by local sequence information.

FIG. 1 illustrates an overview flow diagram of example operations for predicting DNA accessibility using RNA-seq data in accordance with an embodiment. In flow diagram 100, a training dataset of genomic sample data comprising RNA-seq expression data files 102, DNA sequence data for all DNase I hypersensitivity (DHS) sites 104, and DNase-seq data files 106 for a plurality of cell types is used to train a neural network 108 to predict DNA accessibility based on RNA-seq data. As described in further detail below, neural network 108 is configured to process a first input comprising DNA sequence data and a second input comprising gene expression levels derived from RNA-seq data, where input DNase-seq and RNA-seq data files are paired based on a same biotype. In accordance with the embodiments herein, a plurality of batches of paired DNase-seq and RNA-seq data files are used to train neural network 108. Once the training is completed, the neural network trained for predicting DNA accessibility 110 can be configured to receive RNA-seq data 112 and whole genome sequencing 114 for a new genomic sample input with respect to the training dataset, and predict DNA accessibility in the new genomic sample input 116.

Figure 2:
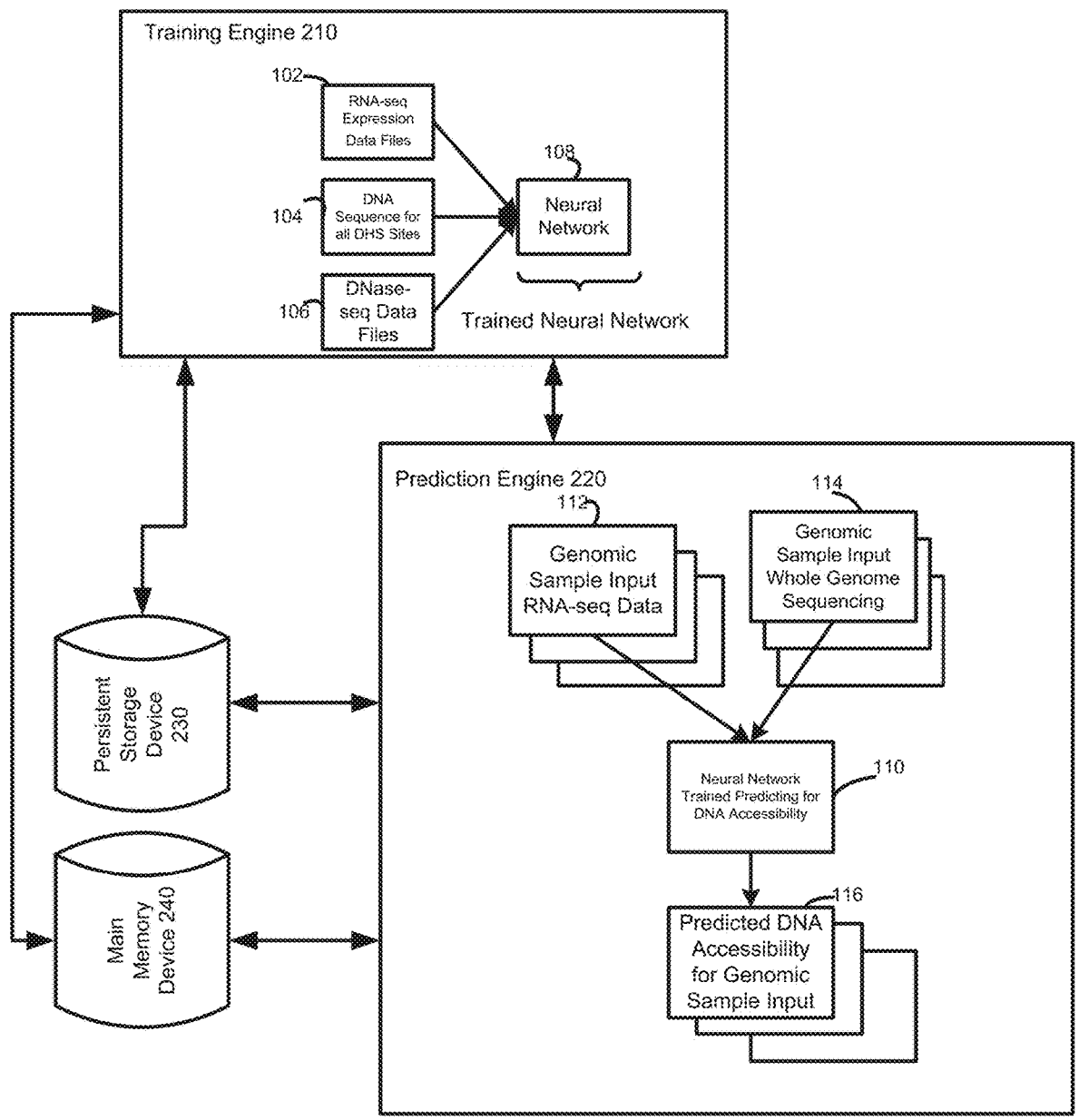
FIG. 2 illustrates a block diagram of a system for predicting DNA accessibility using RNA-seq data in accordance with an embodiment.

FIG. 2 illustrates a block diagram of a system for predicting DNA accessibility using RNA-seq data in accordance with an embodiment. In block diagram 200, elements for predicting DNA accessibility in a genomic sample include a training engine 210, a prediction engine 220, a persistent storage device 230, and a main memory device 240. In an embodiment, training engine 210 may be configured to obtain genomic sample data related to a plurality of cell types, including RNA-seq expression data files 102, DNA sequence data for all DNase I hypersensitivity (DHS) sites 104, and DNase-seq data files 106, from either one or both of persistent storage device 230 and main memory device 240. Training engine 210 may then configure and train neural network 108, which may be stored in either one or both of persistent storage device 230 and main memory device 240, using the genomic sample data; and configure prediction engine 220 to use the trained neural network to predict DNA accessibility in a genomic sample input comprising RNA-seq data and whole genome sequencing for a new cell type with respect to the genomic sample data. For example, prediction engine 220 may obtain RNA-seq data 112 and whole genome sequencing 114 for a new genomic sample input, and predict DNA accessibility in the genomic sample input 116 using the neural network trained for predicting DNA accessibility 110, which may be stored in either one or both of persistent storage device 230 and main memory device 240.

However, it should be noted that the elements in FIG. 2, and the various functions attributed to each of the elements, while exemplary, are described as such solely for the purposes of ease of understanding. One skilled in the art will appreciate that one or more of the functions ascribed to the various elements may be performed by any one of the other elements, and/or by an element (not shown) configured to perform a combination of the various functions. Therefore, it should be noted that any language directed to a training engine 210, a prediction engine 220, a persistent storage device 230 and a main memory device 240 should be read to include any suitable combination of computing devices, including servers, interfaces, systems, databases, agents, peers, engines, controllers, modules, or other types of computing devices operating individually or collectively to perform the functions ascribed to the various elements. Further, one skilled in the art will appreciate that one or more of the functions of the system of FIG. 2 described herein may be performed within the context of a client-server relationship, such as by one or more servers, one or more client devices (e.g., one or more user devices) and/or by a combination of one or more servers and client devices.

Figure 3:
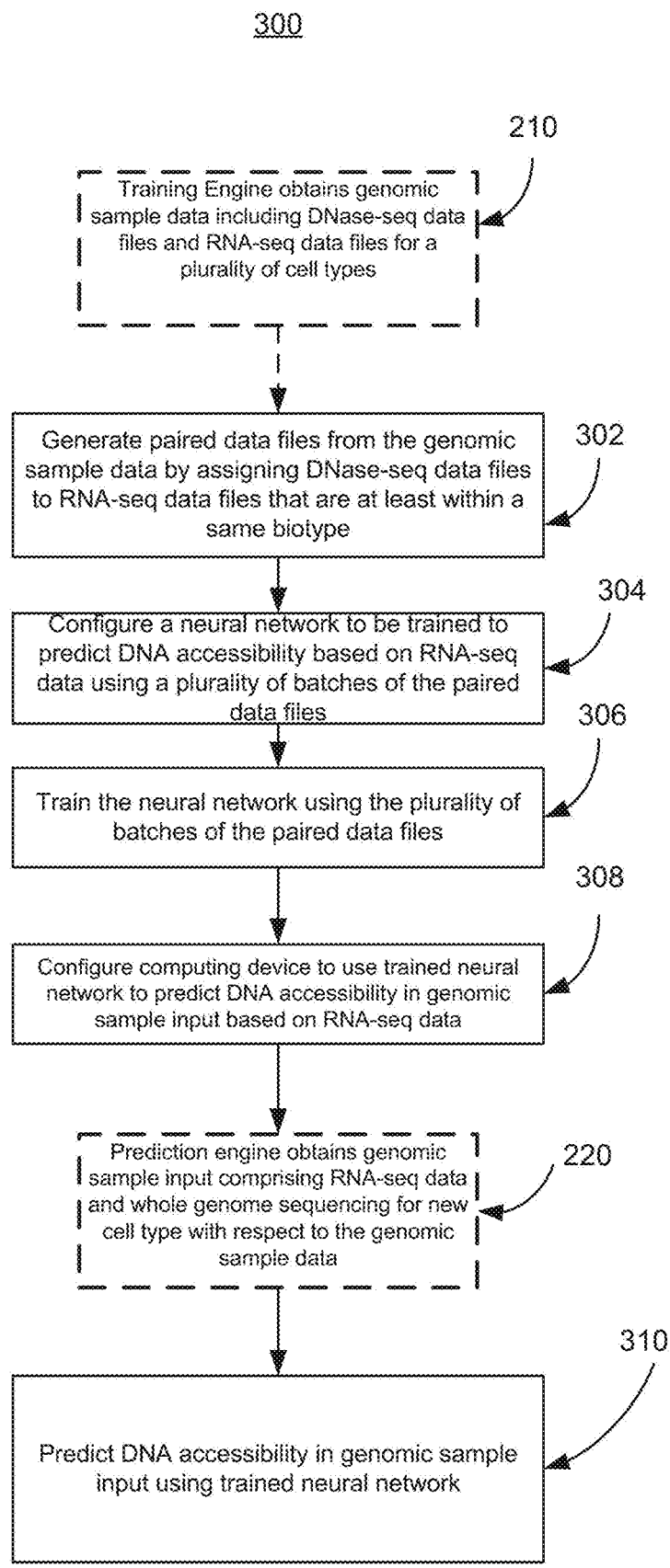
FIG. 3 illustrates a flow diagram of example operations for predicting DNA accessibility in a genomic sample in accordance with an embodiment.

FIG. 3 further illustrates a flow diagram of example operations for predicting DNA accessibility in a genomic sample in accordance with an embodiment. In flow diagram 300, training engine 210 obtains genomic sample data including DNase-seq data files and RNA-seq data files for a plurality of cell types.

To train a neural network for predicting DNA accessibility in the context of gene expression levels, it is necessary to build a genomic sample dataset where both DNase-seq and RNA-seq are both available for a large and diverse collection of different cell types. The genomic sample data may be obtained from any human genomic data source, including from the Encyclopedia of DNA Elements (ENCODE) project consortium or the National Institutes of Health Roadmap Epigenomics mapping consortium databases. For example, to capture a greater diversity of biosample types, RNA-seq data files selected from the ENCODE project database may include files having one or more of "RNA-seq", "polyA mRNA", "polyA depleted", and "single cell" ENCODE labels. In some embodiments, RNA-seq data files that include ENCODE "ERROR" audit flags may be removed from the sample data. However, files with "insufficient read depth," and "insufficient read length" warnings may be kept. While warning files have been characterized as being below ENCODE project standards, the available read depths and lengths in warning situations may be less of an issue when it comes to differentiating cell types. Further, it may be desirable in certain instances to accept more potential noise in favor of a larger diversity of sample types.

In an embodiment, the genomic sample dataset is prepared for training a neural network to predict DNA accessibility based on RNA-seq data by generating a set of paired data files. At step 302, the paired data files are generated from the genomic sample data by assigning DNase-seq data files to RNA-seq data files that are at least within a same biotype. For example, the paired data files may be generated by assigning DNase-seq data files to RNA-seq data files based on matching biosample accessions. The paired data files also may be generated by randomly assigning a DNase-seq data file to one of a plurality of RNA-seq data files determined to be within a same biotype, e.g., in cases where a DNase-seq data file is determined to match several RNA-seq data files. In cases where multiple exact matches of biosample accession exist between the two file types, associations may be restricted to such exact matches. However, if exact match biosample accessions do not exist, RNA-seq and DNase-seq files may be associated based on being from, for example, at least one of a same tissue sample, same cell line, or same patient. Biotypes for which no such correspondences exist may be eliminated from the sample data. In addition, for the purposes learning non-trivially invertible aspects of noise on the neural network, e.g., during testing, both technical and biological replicates may be treated as independent samples of the same biotype. One skilled in the art will appreciate that further refinements of the paired dataset are possible, such as, for example, refinement due to quality concerns and various updates to the dataset, e.g., ENCODE consortium updates.

At step 304, a neural network is configured to be trained to predict DNA accessibility based on RNA-seq data using a plurality of batches of the paired data files. For the embodiments described herein, and as further described below, the neural network for predicting DNA accessibility based on RNA-seq data includes a hierarchical structure comprising a plurality of convolutional layers each succeeded by a max-pooling layer. The neural network further includes at least two fully connected layers following the hierarchical structure. For example, the neural network may comprise a deep convolutional neural network, or a densely connected convolutional neural network.

In an embodiment, configuring the neural network comprises configuring the convolutional layers to process a first input comprising DNA sequence data from one of the paired data files to generate a convolved output, and the fully connected layers following the convolutional layers to concatenate the convolved output with a second input comprising gene expression levels derived from RNA-seq data from the one of the paired data files and process the concatenation to generate a DNA accessibility prediction output. There are many possible strategies for selecting the subset of genes used for the gene expression levels derived from RNA-seq data. In an exemplary embodiment, the Library of Integrated Network-based Cellular Signatures (LINCS) curated L1000 dataset may be used as a subset of genes. However, the subset of genes may be selected using other means including, for example, an autoencoder that leverages a more complete set of genes may be utilized instead of a manually curated subset, such as the L1000 dataset.

The neural network is trained using the plurality of batches of the paired data files at step 306. For example, during training, data may be balanced per batch due to a selected ratio of negative training examples to positive training examples. Each batch may sample an equal amount of accessible and non-accessible sites without replacement, such that one pass through all available negative training examples constitutes multiple randomly permuted passes through all positive training examples. In situations where a DNase-seq file has a plurality of matching RNA-seq files, sites from the DNase-seq file may be randomly assigned to one of the plurality of corresponding RNA-seq expression vectors (derived gene expression levels) each time they are selected for a training batch.

In an embodiment, the batches of the paired data files may include a validation set for evaluating training progress. For example, a plurality of random samples may be selected from each of accessible and non-accessible sites per validation DNase-seq file and used to estimate an Area Under the Receiver Operating Characteristic curve (ROC AUC) throughout training. Prediction performance across whole genomes (i.e., all potential DHS sites) of all validation samples also may be evaluated. In cases where multiple RNA-seq file matches exist, predictions across the entire genome may be evaluated once for every possible DNase-seq and RNA-seq file pair, e.g., to characterize performance as captured by Precision Recall area under curve (PR AUC), which can be less misleading in the presence of data imbalance. Results on test sets may be evaluated across whole genomes following the same procedure.

In an exemplary training embodiment, the paired data files may comprise a plurality of unique biotypes and be partitioned into training, validation, and test sets as illustrated in Table 1.

TABLE 1

Number of file types per dataset partition

| Partition | DNase-seq files | RNA-seq files |
|---|---|---|
| Validation set | 11 | 12 |
| Train set 1 | 195 | 277 |
| Train set 2 | 198 | 281 |
| Test set 1 | 14 | 15 |
| Test set 2 | 11 | 11 |

For the partitions shown in Table 1, the validation set may be held constant, while the training and test sets may include a plurality of variations. For example, the first test set may comprise randomly held-out samples, while the second test set may be selected such that all samples in the test set are from biotypes not represented in the training or validation data, e.g., to accurately simulate the application of the neural network described in the various embodiments herein.

In an embodiment, a greedy merge methodology may be used on all DNase-seq samples in the training sets to obtain a set of all potential sites of accessible DNA along the whole genome. For example, a fixed length, e.g., 600 base pairs centered around a DHS peak, may be used to define each site. Blacklisted sites, i.e., sites at which measurements have been deemed unreliable, may be excluded. The sequence for each genomic site may be obtained from a human genome database, e.g., the Genome Reference Consortium's human genome assembly hg19.

In an embodiment, a dynamic decay rate for the sequence of neural network layers may be configured to be increased over a course of training when moving averages are updated for batch normalization, and one or more network parameters of the sequence of neural network layers may be configured to be optimized based on an adaptive moment estimation (Adam) optimization algorithm.

At step 308, a computing device, e.g., prediction engine 220, is configured to use the trained neural network to predict DNA accessibility in a genomic sample input based on RNA-seq data for a new cell type with respect to the genomic sample (training) data. In an embodiment, the genomic sample input may be associated with a cancer cohort from The Cancer Genome Atlas (TCGA) or a tumor. For example, the cancer cohorts may include one or more of Lung Adenocarcinoma (LUAD), Lung Squamous Cell Carcinoma (LUSC), Kidney Chromophobe (KICH), Kidney Clear Cell Carcinoma (KIRC), Kidney Papillary Cell Carcinoma (KIRP), and Breast Cancer (BRCA). Once configured, prediction engine 220 in operation may obtain a genomic sample input comprising RNA-seq data and whole genome sequencing for a new cell type with respect to the genomic sample data and, at step 310, predict DNA accessibility in the genomic sample input using the trained neural network.

Figure 4:
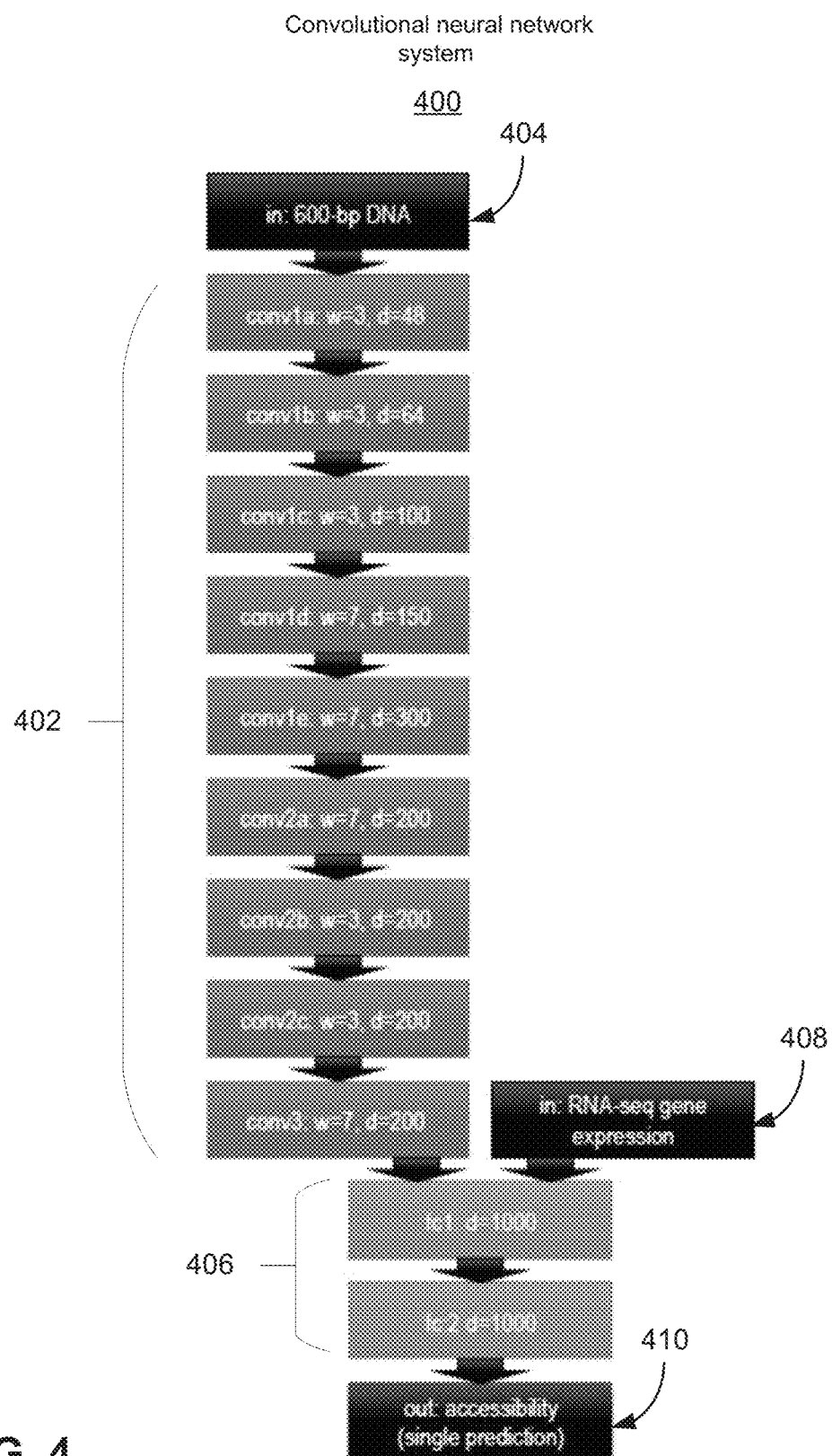
FIG. 4 illustrates a block diagram of a convolutional neural network system for predicting DNA accessibility in a genomic sample in accordance with an embodiment.

FIG. 4 illustrates a block diagram of a convolutional neural network system for predicting DNA accessibility in a genomic sample in accordance with an embodiment. Convolutional neural network system 400 includes a sequence of neural network layers comprising a hierarchical structure 402 comprising a plurality of convolutional layers each succeeded by a max-pooling layer.

The hierarchical structure 402 is configured to receive a first input 404 comprising DNA sequence data from a paired data file and process the first input to generate a convolved output. In an embodiment, first input 404 may be a 600 base-pair segment of DNA represented as a one-hot code (code having a single high ("1") bit and all other values low ("0")). The paired data file, as described above, is generated from genomic sample data for a plurality of cell types by assigning DNase-seq data files to RNA-seq data files that are at least within a same biotype. In an embodiment, the hierarchical structure 402 may comprise at least three convolutional layers (as shown), which apply a specified number of convolution filters to the data and, for each sub-region of the data, perform a set of mathematical operations to produce a single value in an output. Further, the first and second convolutional layers may be factorized to improve the rate of learning and final accuracy of system 400.

At least two fully connected layers 406 follow the hierarchical structure 402 to perform a classification on the features extracted by the convolutional layers and downsampled by the pooling layers. In an embodiment, the at least two fully connected layers 406 are configured to concatenate the convolved output generated by the hierarchical structure 402 with a second input 408 comprising gene expression levels derived from RNA-seq data from the paired data file and process the concatenation to generate a single DNA accessibility prediction output 410.

As described above, the sequence of neural network layers may be trained to predict DNA accessibility based on RNA-seq data using a plurality of batches of paired data files. For example, batch normalization may be utilized at all layers, and a max norm constraint may be applied for regularization of all weights during the course of training. Further, a dynamic decay rate may be used for the sequence of neural network layers for the purposes of achieving competitive performance more quickly than a fixed decay rate. For example, the dynamic decay rate may be configured to increase over a course of training when moving averages are updated for batch normalization. In addition, an adaptive moment estimation (Adam) optimization algorithm, or one or more other optimization algorithms (e.g., RMSProp), may be used to optimize one or more network parameters of the sequence of neural network layers.

While the neural network system illustrated in FIG. 4 is exemplary for implementing the embodiments herein, one skilled in the art will appreciate that various other neural network architectures (e.g., densely connected convolutional networks and Long Short-Term Memory Units (LSTMs)) and additions (such as attention mechanisms) may be utilized. As such, neural network system 400 should not be construed as being strictly limited to the embodiments described herein.

Figure 5:
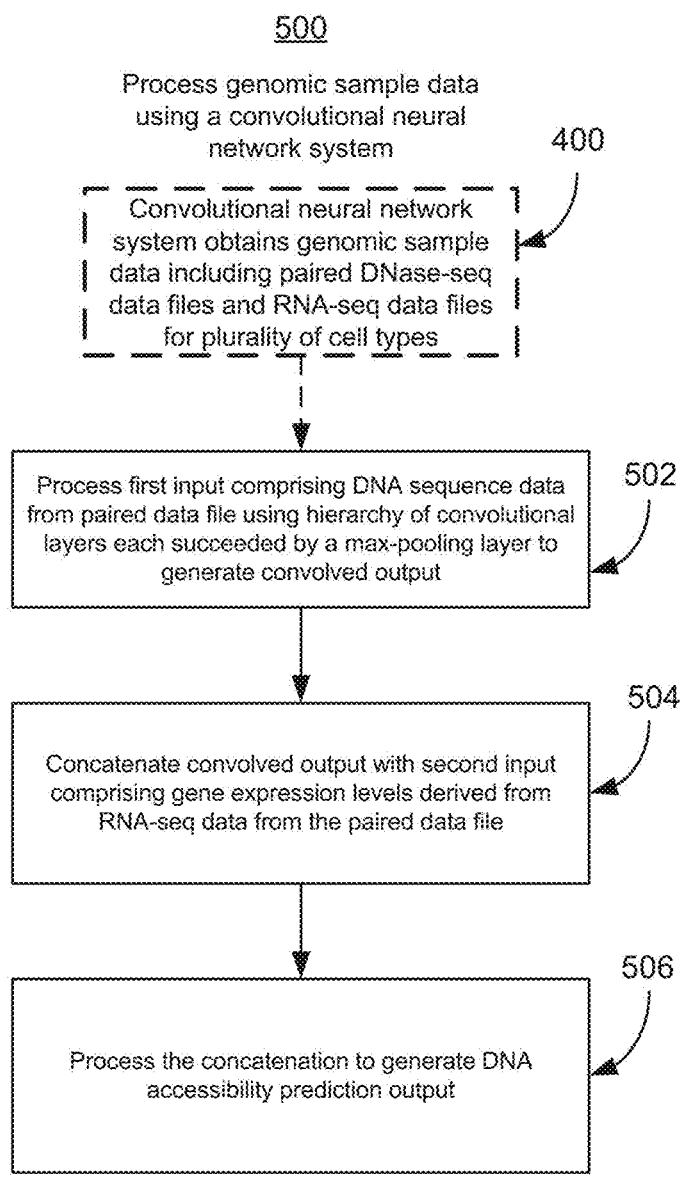
FIG. 5 illustrates a flow diagram of a method of processing genomic sample data for a plurality of cell types using a convolutional neural network system in accordance with an embodiment.

FIG. 5 illustrates a flow diagram of a method of processing genomic sample data for a plurality of cell types using the neural network system of FIG. 4. For example, neural network system 400 may receive genomic sample data including DNase-seq data files and RNA-seq data files for plurality of cell types or, when trained, a genomic sample input comprising RNA-seq data and whole genome sequencing for a new cell type with respect to the genomic sample data.

At step 502, a first input comprising DNA sequence data from a paired data file is processed using a hierarchical structure comprising a plurality of convolutional layers (e.g., a layer which applies a specified number of convolution filters to the data and, for each sub-region of the data, performs a set of mathematical operations to produce a single value in an output) each succeeded by a max-pooling layer (e.g., a layer in which a down-sampling max filter is applied to sub-regions of the initial representation) to generate a convolved output. In an embodiment, the paired data file is generated from the genomic sample by assigning DNase-seq data files to RNA-seq data files that are at least within a same biotype.

At step 504, at least two fully connected layers (i.e., layers in which every node in the layer is connected to every node in the preceding layer) are configured to concatenate the convolved output with a second input comprising gene expression levels derived from RNA-seq data from the paired data file. At step 506, the at least two fully connected layers process the concatenation to generate a single DNA accessibility prediction output.

Test Results

Several alternative versions of neural network system 400 were trained for testing purposes. For comparison purposes, cell-specific models were trained and evaluated following the procedure of the Basset neural network. DNase-seq peak data from 164 sample types obtained from the ENCODE and Roadmap Epigenomics projects was used for cell-specific model training, and a universal set of potential accessibility sites was created by a greedy merging of overlapping peaks across all DNase-seq data samples. For each site, a binary vector was used to label its accessibility state in each of the 164 cell types. The data was then split by genomic site so that 70,000 peak locations were held out for validation, 71,886 for testing, and the remaining 1.8 million sites were used for training.

Figure 6:
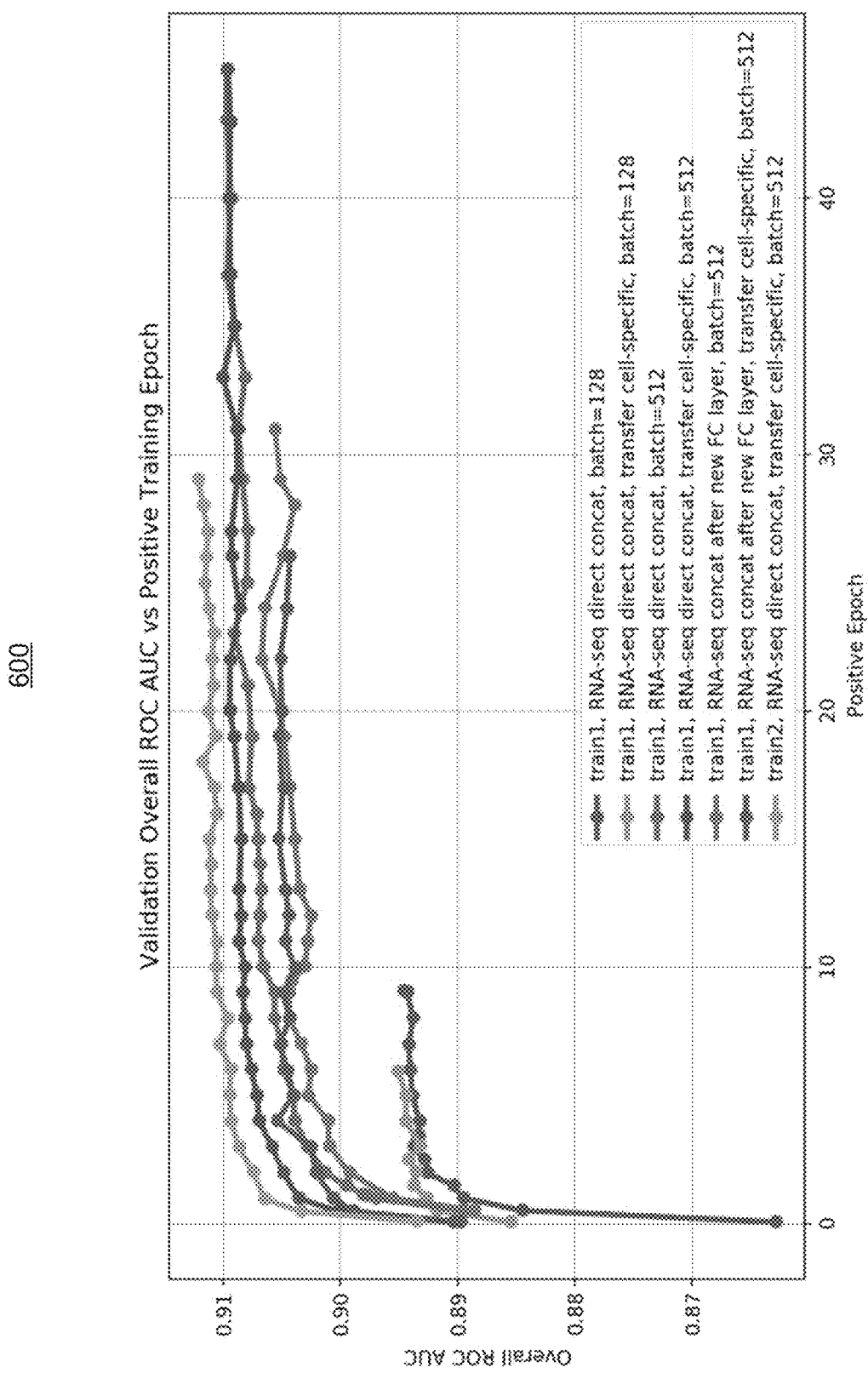
FIG. 6 illustrates a graphical representation of overall ROC AUC results for a validation dataset in accordance with an embodiment.

FIG. 6 illustrates overall ROC AUC for the small validation set over number of passes through all positive examples (positive epochs) for various model architectures using RNA-seq input. Graph 600 illustrates the results from an experiment that added a fully connected (FC) layer of depth 500 before concatenating gene expressions with outputs from the convolutional layers. However, increasing the batch size and initializing the convolutional layers with weights from the final cell-specific model (transfer) improved performance most. Models trained on set 1 showed similar validation performance as those trained on set 2 with the same hyperparameters. This evaluation was done before the final dataset revision which revoked several suspected low-quality samples, yet still provided valuable feedback for model selection.

Figure 7:
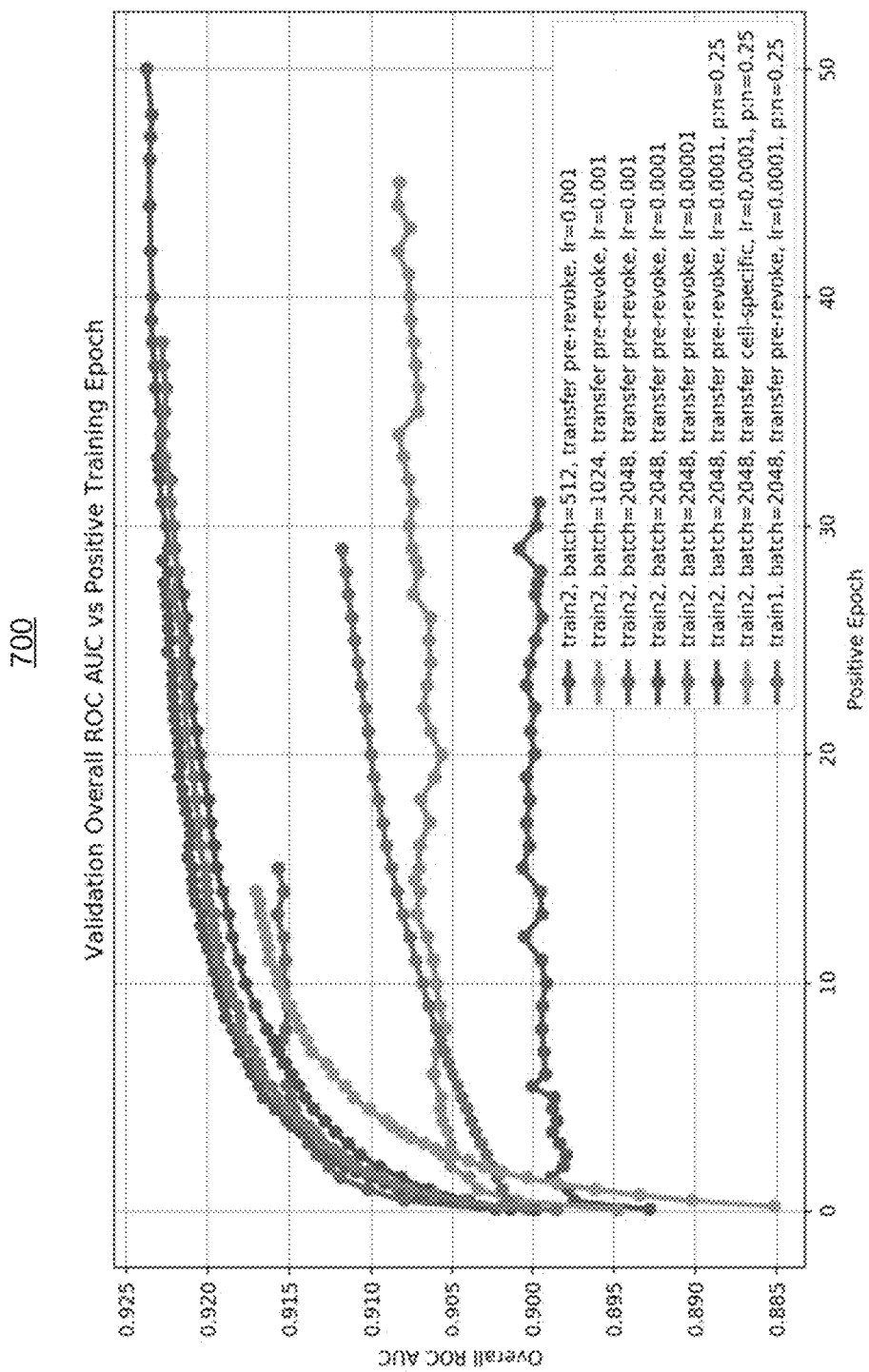
FIG. 7 illustrates a graphical representation of overall ROC AUC results for a validation dataset after final dataset revision in accordance with an embodiment.

FIG. 7 illustrates overall ROC AUC for the small validation set over positive training epochs for models trained after the final dataset revision. Graph 700 illustrates that a further increase in batch size as well as a decreased learning rate led to additional significant improvements. Changing the fraction of positive samples per training batch (from 0.5 to 0.25) also slightly improved both ROC AUC as well as PR AUC in whole genome validation. The transfer of weights learned before final revoking of data (FIG. 6) was a more effective initialization than transfer learning from the final cell-specific model. It was also confirmed that the same hyperparameters led to good validation performance across both training partitions.

Over the course of training, as reported in the validation results of FIGS. 6 and 7, it was found that adding a fully connected layer before concatenating RNA-seq data to output from the convolutional layers performed consistently worse than direct concatenation without the fully connected layer. Further, transfer learning consistently shortened the training time across model variants. However, the most impactful changes included increasing the batch size (from 128 to 512, and finally to 2048), and decreasing the learning rate (from 0.001 to 0.0001).

The cell-specific models had multi-task outputs so that each training sample provided an information rich gradient based on multiple labels for backpropagation. However, using RNA-seq inputs in neural network system 400 eliminated the need for multi-task outputs, so each sample only provided gradient feedback based on a single output. The batch size increase was thus intended to compensate for this change in output dimension to produce a more useful gradient for each batch.

The learning rate decrease, on the other hand, was guided by the observation that training was reaching a point of slow improvement before even a single full pass through all negative training examples. The new dataset was also significantly larger than that used to train cell-specific models. In transfer learning using weights learned from the corresponding data splits before final cleanup of revoked files was more effective on the final data than transfer of convolutional layer weights from the best cell-specific model. Since some of the revoked samples featured a very high rate of DHS peaks, the pre-revoke dataset included many more sites of interest (2.7 million). This meant that aside from many additional negative examples, a fair number of potentially accessible sites also had differently centered peaks. However, this added positional noise may have encouraged model robustness.

Neural network system 400, as illustrated in FIG. 4, was initialized with weights learned from the prior iteration of the dataset, before the final revoked files were removed. In turn, those models were initialized with convolutional layer parameters from the best performing cell-specific model. An effective batch size of 2048 was used for training (two GPUs processing distinct batches of 1024), with an Adam learning rate of 0.0001 and a 0.25 fraction of positive to negative samples in every batch.

Table 2 shows that final neural network system performance on the validation set, both overall and by biotype, was consistent across each of the two training partitions with respect to both ROC AUC as well as PR AUC.

TABLE 2

Whole genome validation results for final neural network system trained on set 1 (t1) and set 2 (t2)

| Sample biotype | ROC AUC (t1) | PR AUC (t1) | ROC AUC (t2) | PR AUC (t2) |
| --- | --- | --- | --- | --- |
| CD14-positive monocyte | 0.888 | 0.559 | 0.889 | 0.563 |
| muscle of arm | 0.774, 0.959 | 0.654, 0.808 | 0.783, 0.960 | 0.671, 0.811 |
| fibroblast of arm | 0.898, 0.900 | 0.806, 0.809 | 0.898, 0.900 | 0.808, 0.811 |
| SJCRH30 | 0.875 | 0.727 | 0.875 | 0.730 |
| foreskin fibroblast | 0.953 | 0.774 | 0.953 | 0.771 |
| right renal pelvis | 0.967 | 0.833 | 0.968 | 0.836 |
| spinal cord | 0.947 | 0.714 | 0.946 | 0.713 |
| Panc1 | 0.957 | 0.713 | 0.958 | 0.711 |
| right lung | 0.958 | 0.781 | 0.958 | 0.782 |
| A549 | 0.902 | 0.735 | 0.900 | 0.734 |
| mean biotype AUC | 0.915 | 0.743 | 0.916 | 0.745 |
| overall AUC | 0.912 | 0.721 | 0.913 | 0.725 |

Table 3 and Table 4 summarize the results of applying neural network system 400 across whole genomes, at all potential DHS sites. For biotypes with more than a single file pair in the test set, each sample's results are listed.

TABLE 3

Test set 1 whole genome results

| Sample biotype | ROC AUC | PR AUC |
| --- | --- | --- |
| A172 | 0.959 | 0.721 |
| left renal pelvis | 0.967 | 0.838 |
| small intestine | 0.951, 0.926 | 0.737, 0.571 |
| muscle of arm | 0.968 | 0.843 |
| forelimb muscle | 0.968 | 0.808 |
| keratinocyte | 0.939 | 0.644 |
| skin fibroblast | 0.948, 0.947 | 0.770, 0.763 |
| large intestine | 0.964 | 0.727 |
| muscle of back | 0.967, 0.954 | 0.853, 0.854 |
| adrenal gland | 0.957 | 0.743 |
| SK-N-DZ | 0.898 | 0.652 |
| fibroblast of lung | 0.942 | 0.840 |
| mean biotype AUC | 0.950 | 0.758 |
| overall AUC | 0.947 | 0.748 |

TABLE 4

Test set 2 whole genome results

| Sample biotype | ROC AUC | PR AUC |
| --- | --- | --- |
| left kidney | 0.965 | 0.778 |
| OCI-LY7 | 0.899, 0.899, 0.886, 0.886 | 0.654, 0.654, 0.655, 0.654 |
| prostate gland | 0.865 | 0.516 |
| hindlimb muscle | 0.943 | 0.824 |
| spleen | 0.913 | 0.582 |
| astrocyte | 0.919, 0.944 | 0.787, 0.613 |
| fibroblast of skin of abdomen | 0.964 | 0.826 |
| G401 | 0.739, 0.846 | 0.459, 0.516 |
| mean biotype AUC | 0.898 | 0.655 |
| overall AUC | 0.897 | 0.621 |

Unsurprisingly, system performance was compromised by completely new biotypes, however, even given this more challenging scenario the overall PR AUC was higher than the best cell-specific models evaluated using known biotypes. Note that several of the results in Table 4 were within similar ranges as predictions whose sample types overlapped with training.

To better understand the performance characteristics and limitations of neural network system 400, the ENCODE validation and test results were broken down by genomic site type. Exon, protein coding exon, intragenic, and intergenic regions were derived from annotations defined by GENCODE v19, and promoter and flank region annotations were obtained from ENSEMBL.

Table 5 details the distribution of annotations applied to the 1.71 million sites considered in the held-out biotype training set, as well as the fraction of all positive samples that fall within each annotation type. Note that a single site may overlap with more than one annotation, and that Table 5 only reports details of the held-out biotypes partition (train/test set 2).

TABLE 5

Distribution of potentially accessible sites by annotation

| Site type | Percent of all sites |
| --- | --- |
| exon | 3.47 |
| protein coding exon | 2.75 |
| intragenic | 49.94 |
| intergenic | 39.89 |
| promoter and flank | 6.37 |
| other | 5.39 |

Figure 8:
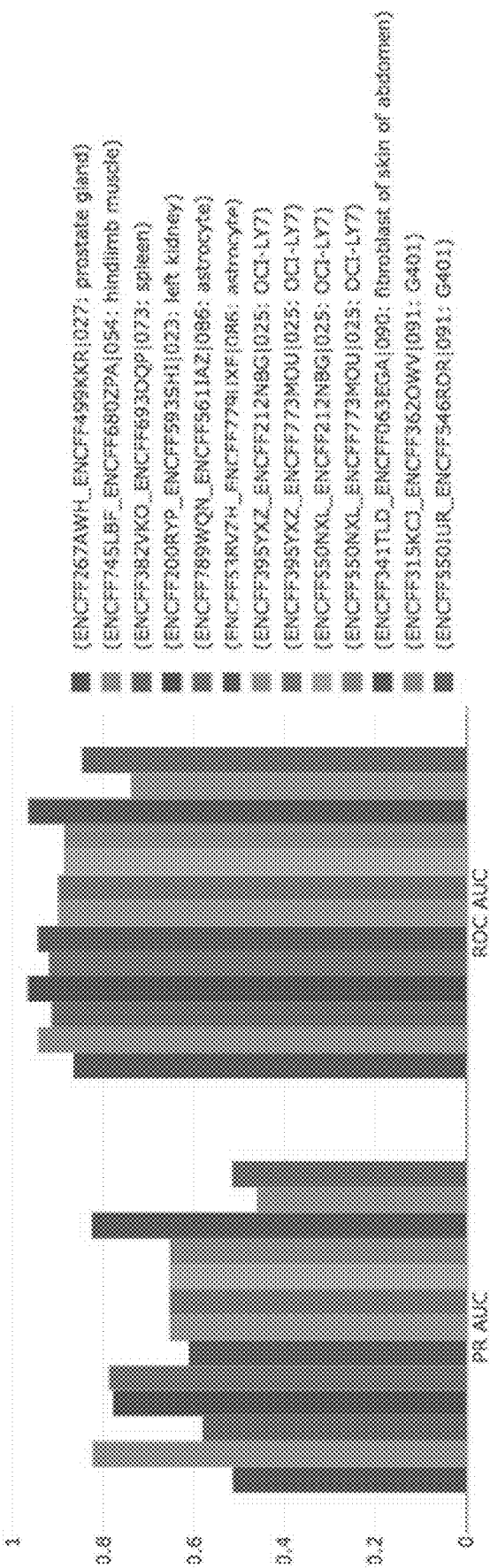
FIG. 8 illustrates a graphical representation of PR AUC and ROC AUC results for a test dataset per whole genome sample in accordance with an embodiment.
Figure 9:
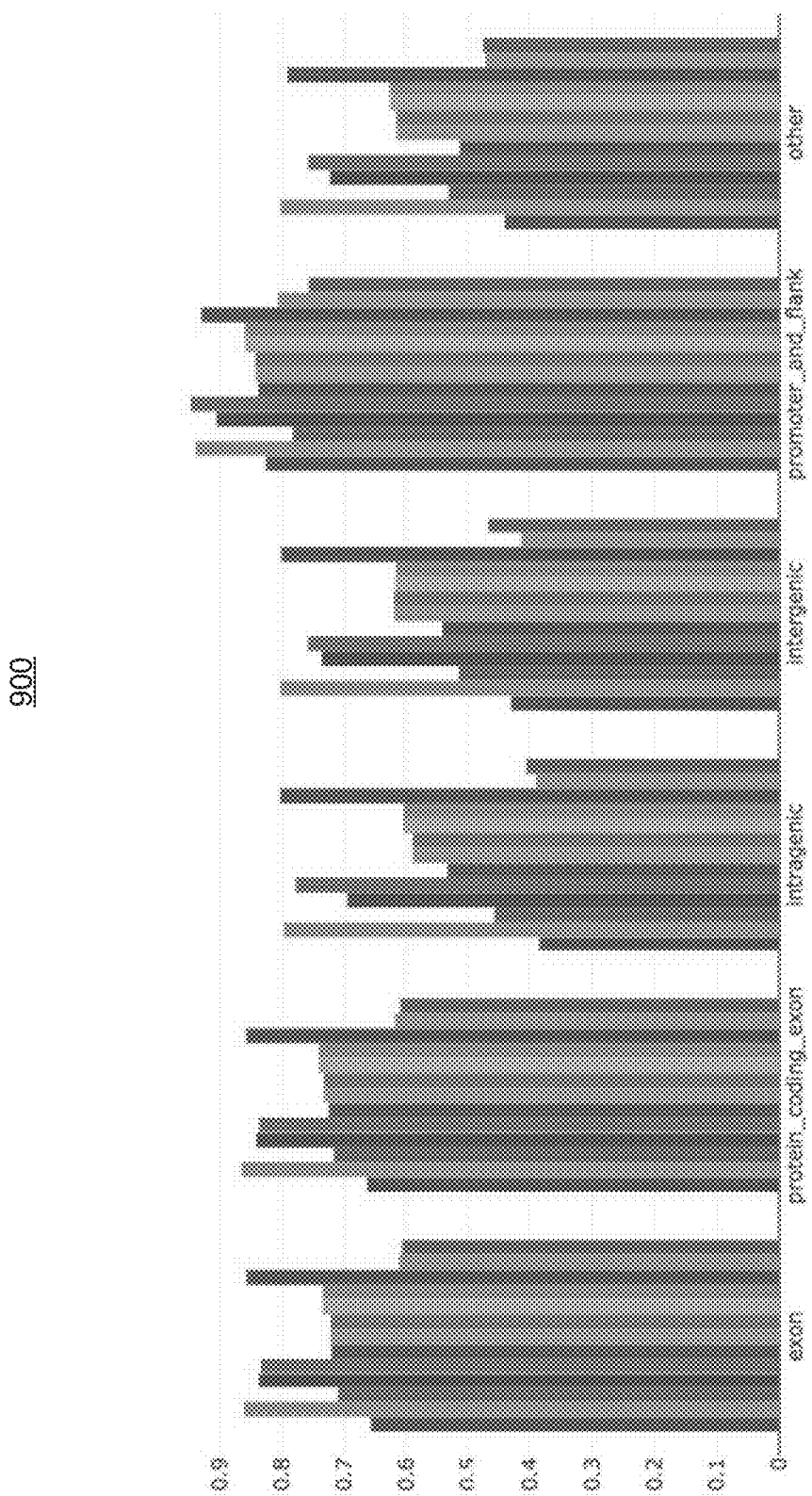
FIG. 9 illustrates a graphical representation of PR AUC results for a test dataset per whole genome sample in accordance with an embodiment.
Figure 10:
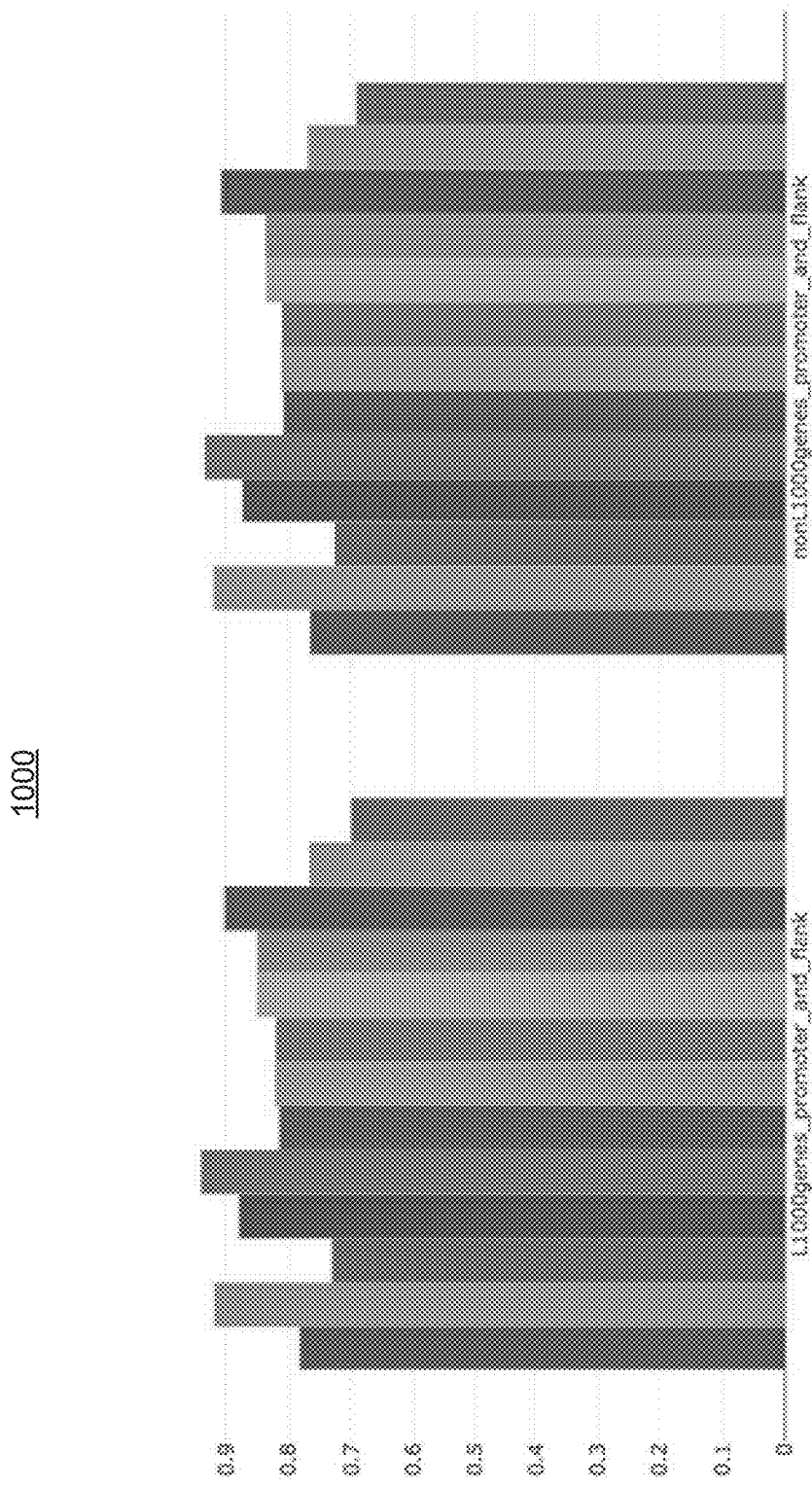
FIG. 10 illustrates a graphical representation of promoter and flank PR AUC and ROC AUC results for a test dataset per whole genome sample in accordance with an embodiment.

FIGS. 8, 9, and 10 illustrate that even for samples in which the system performed poorly overall, predictions within promoter and flank regions consistently attained a high level of accuracy, achieving PR AUC=0:838 over all held out biotypes (test set 2) and PR AUC=0:908 over randomly held out samples (validation set).

In FIG. 8, graph 800 illustrates PR AUC and ROC AUC results for the test set of held-out biotypes (set 2) per whole genome sample. Since ROC AUC is affected by data imbalance, the PR AUC metric is a better evaluation of whole genome performance.

In FIG. 9, graph 900 illustrates PR AUC results on the test set of held out biotypes (set 2) split per whole genome sample and broken down by genomic site type. As illustrated, performance on promoter and flank regions was consistently high, even for samples where overall results were lowest. Note that graph coloring is the same as defined in the legend of FIG. 8.

Figure 11:
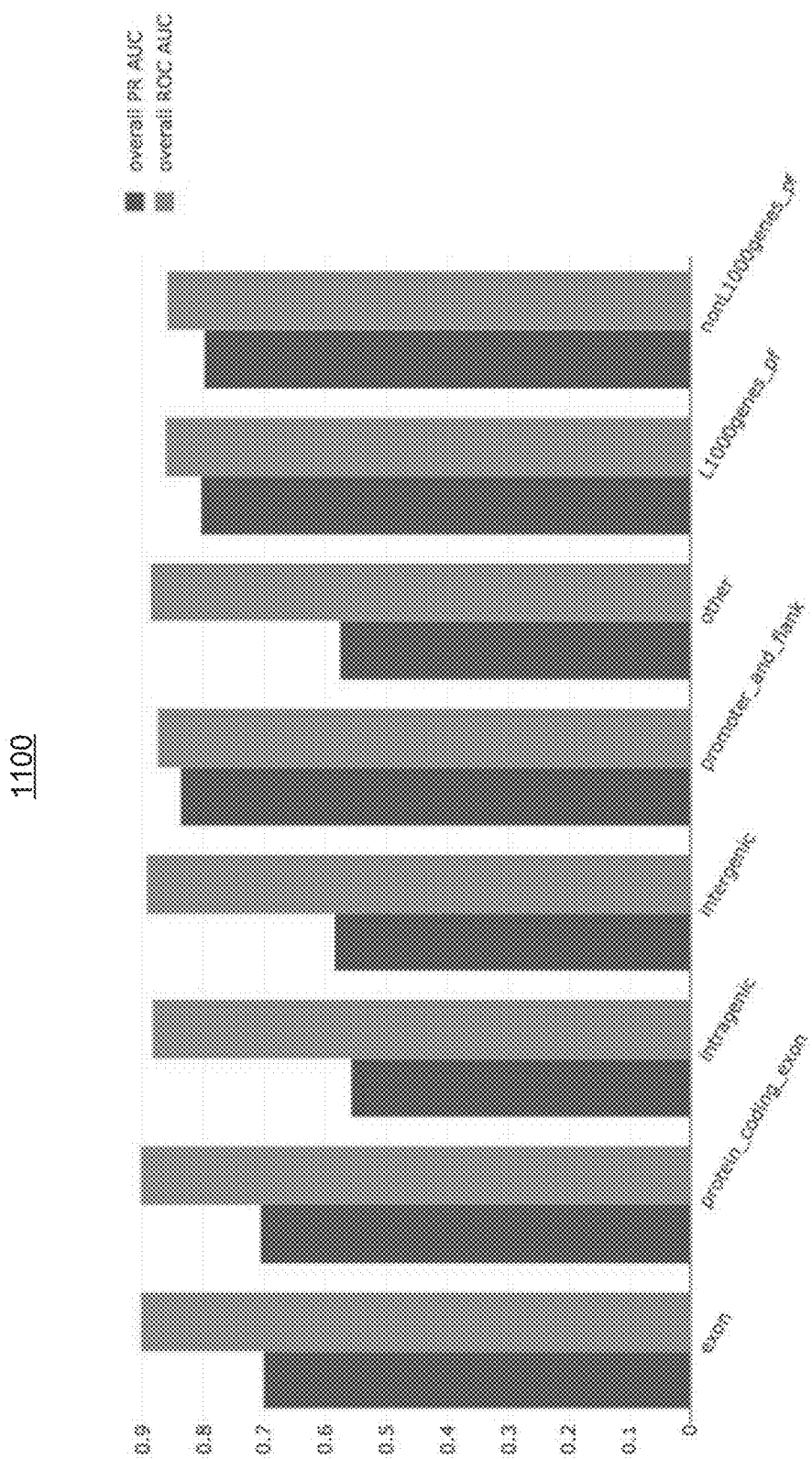
FIG. 11 illustrates a graphical representation of overall PR AUC and ROC AUC results for a test dataset in accordance with an embodiment.

FIGS. 10 and 11 confirm that the accuracy of these predictions was independent of whether the promoter and flank sites overlapped with the regions of genes used in our RNA-seq input vector.

In FIG. 10, graph 1000 illustrates promoter and flank PR AUC results on the test set of held-out biotypes (set 2) split per whole genome sample and broken down by input gene set (L1000) membership. No clear performance difference was observed when promoter and flank regions were split into those that do and do not overlap the RNA-seq input gene set. Note that graph coloring is the same as defined in the legend of FIG. 8.

In FIG. 11, graph 1100 illustrates overall results on the test dataset of held out biotypes (set 2) broken down by site type and L1000 gene set membership.

As shown in FIGS. 10 and 11, selecting a threshold for classification of only promoter and flank sites such that precision is 80% (20% false discovery rate) on the held-out biotype test set, the trained system recalls 65.3% of accessible promoter regions, with a false positive rate of 10%. Moreover, the system achieves a precision of 93.4% when this same threshold is applied to the validation set where biotypes are allowed to overlap with the training set, recalling 62.6% of accessible promoter regions, with a false positive rate of only 3.5%.

Application to the Pan-Cancer Genome

Once trained, the neural network for predicting DNA accessibility described in the various embodiments herein can be applied to new datasets where RNA-seq 112 and whole genome sequence information 114 are available, as illustrated in FIG. 1.

One application of the neural network system is to predict DNA accessibility for samples in the pan-cancer genome. To construct a predicted accessibility profile for each TCGA sample, all somatic SNP, insertion (INS), and deletion (DEL) mutations were applied to any affected sites. However, before looking at the global scope and comparing accessibility profiles, it is helpful to understand the impact of mutations on our set of genomic interest regions.

Figure 12:
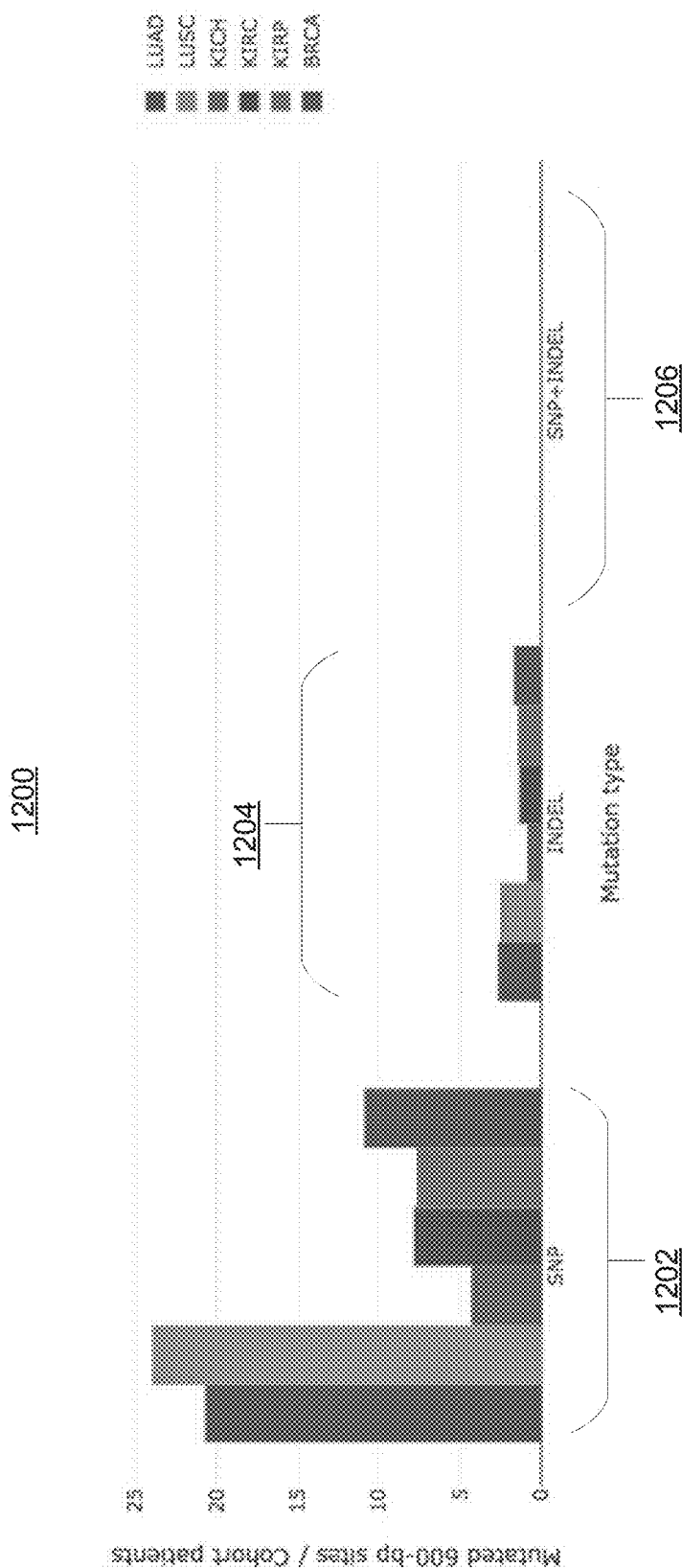
FIG. 12 illustrates a graphical representation mutated promoter and flank sites normalized per number of patients analyzed per cohort in accordance with an embodiment.

In FIG. 12, graph 1200 illustrates the total number of SNP 1202, INDEL 1204, and SNP+INDEL 1206 mutations per cohort, normalized by each cohort's patient count. Across all samples in the above cohorts for whole genome data was available, 3172 interest regions had a single SNP, 78 had 2 SNPs, and only 9 regions had between 3 and 5 SNPs. A total of 465 sites included an insertion or deletion (INDEL) mutation, and there were only 7 sites where both SNP and INDEL mutations occurred together (4 in BRCA, 2 in LUSC, 1 in LUAD). As such, they are hardly visible in this plot.

Figure 13:
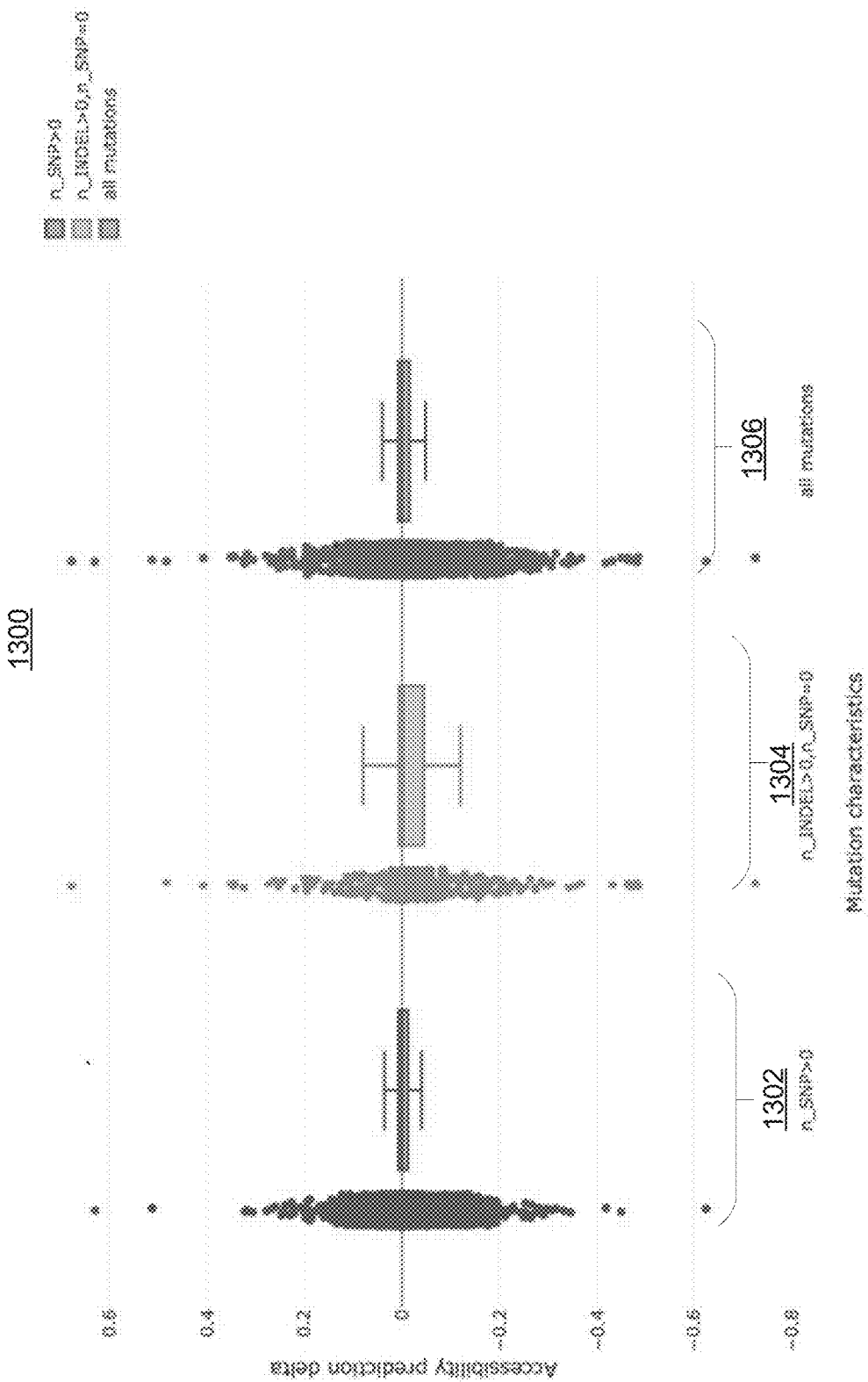
FIG. 13 illustrates a visual representation of box plots showing impact of mutations on predicted accessibility score at 600 base-pair promoter and flank sites in accordance with an embodiment.

For each sample site affected by at least one mutation, the change in predicted accessibility was computed before and after each type of mutation was applied. FIG. 13 illustrates a visual representation of box plots showing impact of mutations on predicted accessibility score at 600 base-pair promoter and flank sites in accordance with an embodiment.

In FIG. 13, plot 1300 shows the distribution of changes due to SNPs only 1302, INDELs only 1304, and all mutations 1306 applied across all samples. INDEL mutations 1304 showed a larger variance in how much they impacted the accessibility score, which is to be expected since they typically impact a greater number of base pairs.

Figure 14:
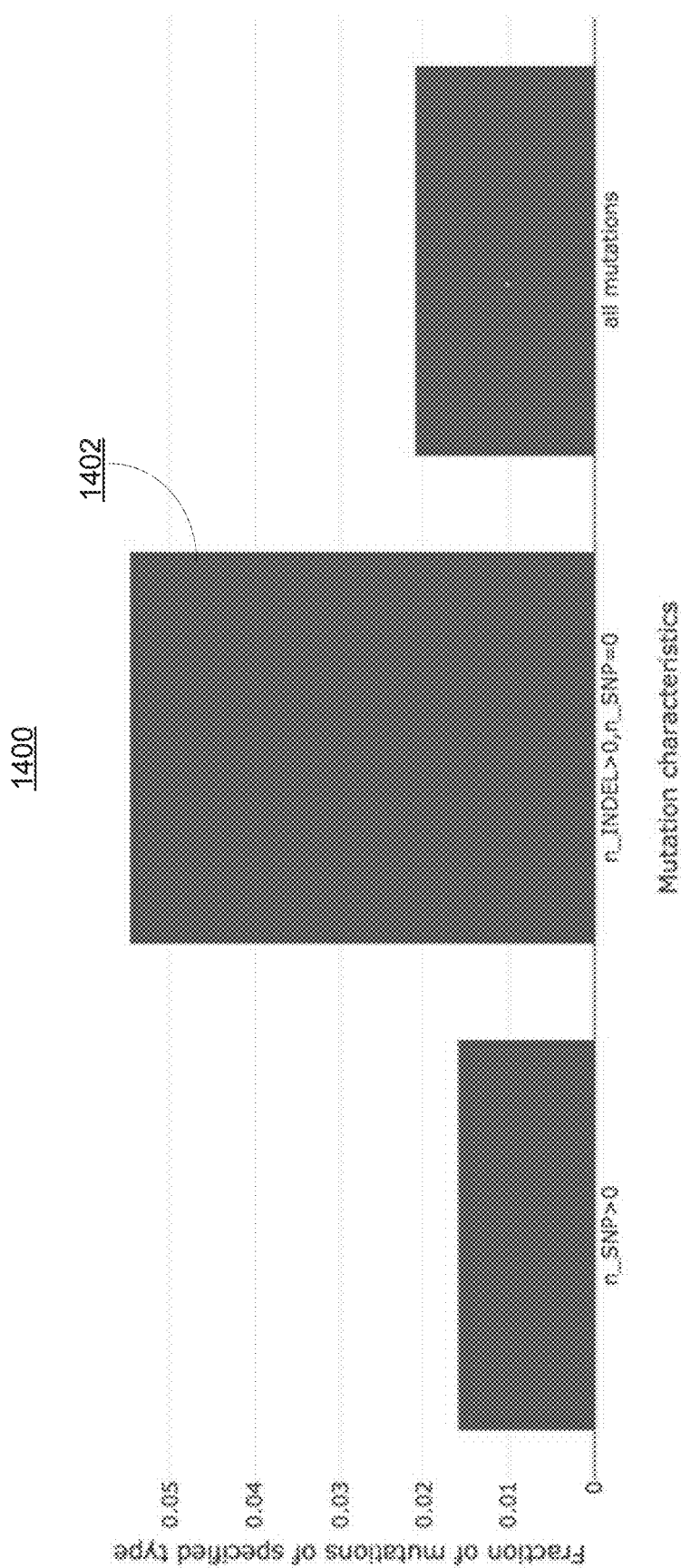
FIG. 14 illustrates a graphical representation of a fraction of mutated sites within a certain category of mutation that ended up flipped versus using the hg19 reference genome in accordance with an embodiment.

FIG. 14 illustrates a graphical representation 1400 of a fraction of mutated sites within a certain category of mutation that ended up flipped versus using the hg19 reference genome in accordance with an embodiment. For graph 1400, it was investigated, applying the 80% precision threshold, how frequently each type of mutation caused accessibility decision changes. Among all mutations that led to changes in classification INS and DEL mutations were the most frequent causes of a decision flip. Notably, of all promoter and flank sites affected by INDELs 1402, 5.46% resulted in changed classification outcomes.

Figure 15:
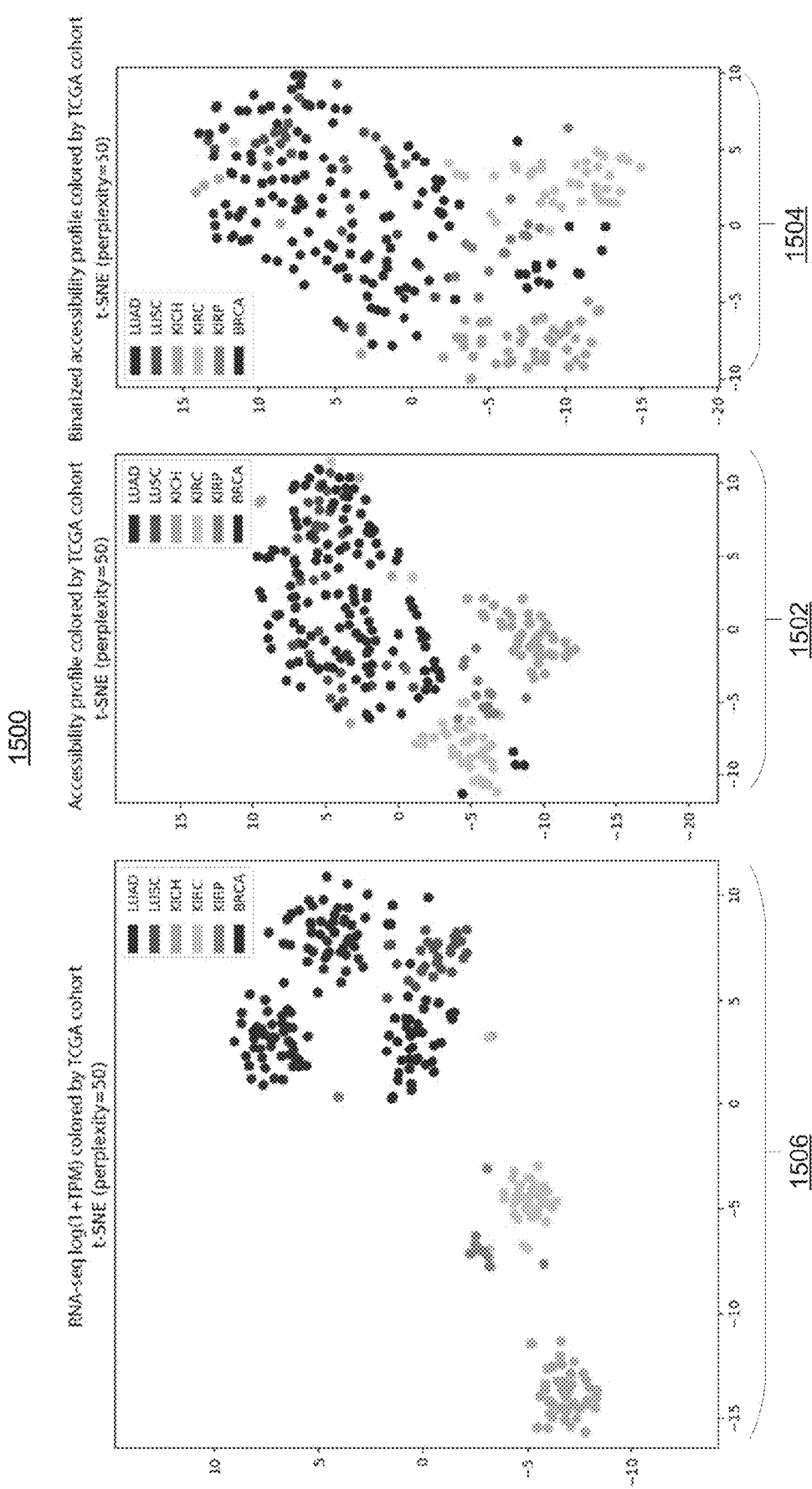
FIG. 15 illustrates a visual representation of DNA accessibility characteristics in accordance with an embodiment.

After applying all mutations, predictions from all promoter and flanks sites were stacked into a single vector per sample to form the accessibility profiles for all the samples in the six TCGA cohorts. FIG. 15 illustrates a visual representation 1500 of accessibility characteristics in accordance with an embodiment. In FIG. 15, a neural network system as described herein was applied to six cancer cohorts: Lung Adenocarcinoma (LUAD), Lung Squamous Cell Carcinoma (LUSC), Kidney Chromophobe (KICH), Kidney Clear Cell Carcinoma (KIRC), Kidney Papillary Cell Carcinoma (KIRP), and Breast Cancer (BRCA) from TCGA. Predictions on the TCGA samples were limited to the subset of potentially accessible sites that overlapped promoter and flank annotations, since performance on those predictions was high across all tests. For consistency with the analysis presented above, all TCGA results were obtained by applying the best model trained on set 2 (held out biotypes). FIG. 15 illustrates a t-Distributed Stochastic Neighbor Embedding (t-SNE) visualization of a Library of Integrated Cellular Signatures (LINCS) L1000 gene expression platform gene expression level vectors from RNA-seq data 1502, raw predicted accessibility profile values 1502, and binarized accessibility profile data 1504 after applying the 80% precision threshold in samples from six TCGA cohorts. In the RNA-seq space 1506, a clear distinction can be seen between basal-like versus luminal AB and HER2-enriched breast cancers (BRCA). In the predicted accessibility spaces (1504 and 1506) the lung (LUAD, LUSC) and breast (BRCA) cancer samples appear to have some common accessibility characteristics. Thus, the relationships between TCGA accessibility profiles visualized using t-SNE in FIG. 15 suggest that looking at cancers from the viewpoint of DNA accessibility offers different relationships and subcategories than RNA-seq.

As such, predictive neural network systems operating on DNA sequence data can learn to handle cell-specific behavior in a way that allows application to new sample types without re-training. The embodiments herein improve on prior cell-specific accessibility prediction, obtaining a mean receiver operating characteristic (ROC) area under the curve (AUC)=0:910 and mean precision-recall (PR) AUC=0:605, compared to the previous mean ROC AUC=0:895 and mean PR AUC=0:561.

Further, the embodiments herein enable accessibility predictions on any new sample for which RNA-seq data is available, without requiring cell-type specific DNase-seq data for re-training. This new neural network system obtained overall PR AUC=0:621 and ROC AUC=0:897 when applied across whole genomes of new samples whose biotypes were held out from training, and PR AUC=0:725 and ROC AUC=0:913 on randomly held out new samples whose biotypes were allowed to overlap with training. Moreover, for promoter and flank regions of the genome the neural network system predicts accessibility to high reliability, achieving PR AUC=0:838 in held out biotypes and PR AUC=0:908 in randomly held out samples. This performance is not sensitive to whether the promoter and flank regions fall within genes used in the input RNA-seq expression vector.

As such, gene expression from RNA-seq can be added as a signature input that allows machine learning to exploit cell-type similarity. A neural network system for predicting DNA accessibility using RNA-seq data can achieve consistently high performance for predictions at promoter and flank regions of the genome, thus enabling a new tool for analysis of tumor genomes across different cell and tissue types and has provided the first glimpse of DNA accessibility (e.g., motor accessibility patterns) across several cohorts from The Cancer Genome Atlas (TCGA).

Systems, apparatus, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computers and interact via a network. The client-server relationship may be defined and controlled by computer programs running on the respective client and server computers.

Figure 16:
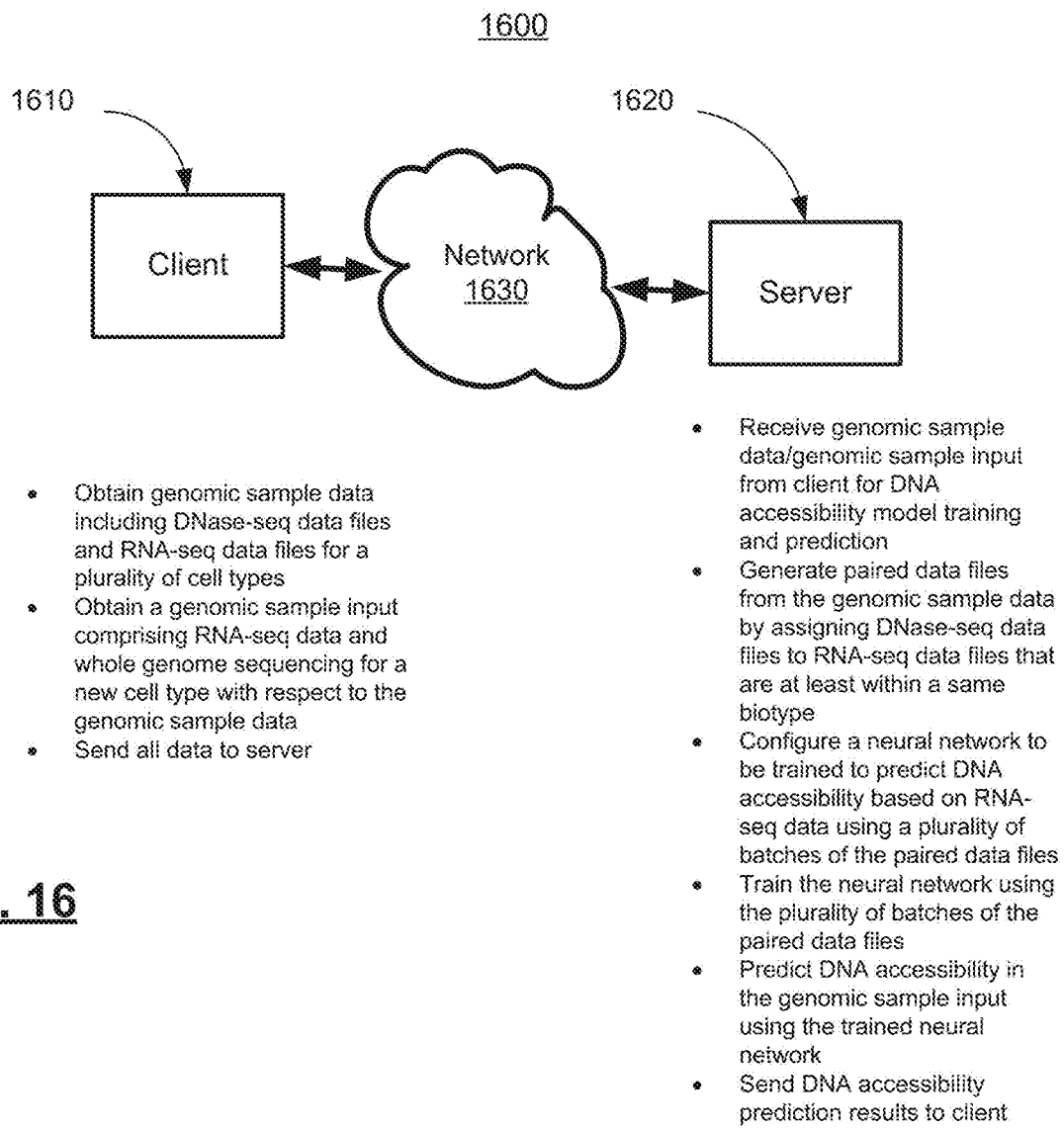
FIG. 16 illustrates a block diagram of an exemplary client-server relationship that can be used for implementing one or more aspects of the various embodiments.

A high-level block diagram of an exemplary client-server relationship that may be used to implement systems, apparatus and methods described herein is illustrated in FIG. 16. Client-server relationship 1600 comprises client 1610 in communication with server 1620 via network 1630, and illustrates one possible division of DNA accessibility prediction tasks between client 1610 and server 1620. For example, client 1610, in accordance with the various embodiments described above, may obtain genomic sample data including DNase-seq data files and RNA-seq data files for a plurality of cell types and send the genomic sample data to server 1620. Server 1620 may, in turn, receive genomic sample data/genomic sample input from client for DNA accessibility neural network training and prediction, generate paired data files from the genomic sample data by assigning DNase-seq data files to RNA-seq data files that are at least within a same biotype, configure a neural network to be trained to predict DNA accessibility based on RNA-seq data using a plurality of batches of the paired data files, and train the neural network to predict DNA accessibility based on RNA-seq data using a plurality of batches of the paired data files. Client 1610 may further send a genomic sample input comprising RNA-seq data and whole genome sequencing for a new cell type with respect to the genomic sample data to server 1620, which may receive the genomic sample input, predict DNA accessibility in the genomic sample input using the trained neural network, and send DNA accessibility prediction results for the genomic sample input to client 1610. One skilled in the art will appreciate that the exemplary client-server relationship illustrated in FIG. 16 is only one of many client-server relationships that are possible for implementing the systems, apparatus, and methods described herein. As such, the client-server relationship illustrated in FIG. 16 should not, in any way, be construed as limiting. Examples of client devices 1610 can include cellular smartphones, kiosks, personal data assistants, tablets, robots, vehicles, web cameras, or other types of computer devices.

Systems, apparatus, and methods described herein may be implemented using a computer program product tangibly embodied in an information carrier, e.g., in a non-transitory machine-readable storage device, for execution by a programmable processor; and the method steps described herein, including one or more of the steps of FIGS. 3 and 5, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 17:
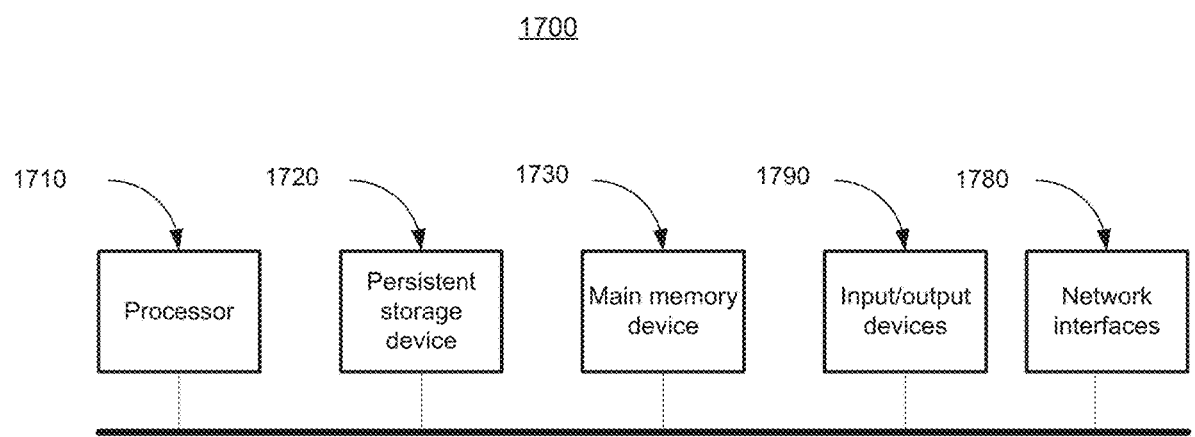
FIG. 17 illustrates a block diagram of a distributed computer system that can be used for implementing one or more aspects of the various embodiments.

A high-level block diagram of an exemplary apparatus that may be used to implement systems, apparatus and methods described herein is illustrated in FIG. 17. Apparatus 1700 comprises a processor 1710 operatively coupled to a persistent storage device 1720 and a main memory device 1730. Processor 1710 controls the overall operation of apparatus 1700 by executing computer program instructions that define such operations. The computer program instructions may be stored in persistent storage device 1720, or other computer-readable medium, and loaded into main memory device 1730 when execution of the computer program instructions is desired. For example, training engine 210 and prediction engine 220 may comprise one or more components of computer 1700. Thus, the method steps of FIGS. 3 and 5 can be defined by the computer program instructions stored in main memory device 1730 and/or persistent storage device 1720 and controlled by processor 1710 executing the computer program instructions. For example, the computer program instructions can be implemented as computer executable code programmed by one skilled in the art to perform an algorithm defined by the method steps of FIGS. 3 and 5. Accordingly, by executing the computer program instructions, the processor 1710 executes an algorithm defined by the method steps of FIGS. 3 and 5. Apparatus 1700 also includes one or more network interfaces 1780 for communicating with other devices via a network. Apparatus 1700 may also include one or more input/output devices 1790 that enable user interaction with apparatus 1700 (e.g., display, keyboard, mouse, speakers, buttons, etc.).

Processor 1710 may include both general and special purpose microprocessors, and may be the sole processor or one of multiple processors of apparatus 1700. Processor 1710 may comprise one or more central processing units (CPUs), and one or more graphics processing units (GPUs), which, for example, may work separately from and/or multi-task with one or more CPUs to accelerate processing, e.g., for various deep learning and analytics applications described herein. Processor 1710, persistent storage device 1720, and/or main memory device 1730 may include, be supplemented by, or incorporated in, one or more application-specific integrated circuits (ASICs) and/or one or more field programmable gate arrays (FPGAs).

Persistent storage device 1720 and main memory device 1730 each comprise a tangible non-transitory computer readable storage medium. Persistent storage device 1720, and main memory device 1730, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 1790 may include peripherals, such as a printer, scanner, display screen, etc. For example, input/output devices 1790 may include a display device such as a cathode ray tube (CRT), plasma or liquid crystal display (LCD) monitor for displaying information (e.g., a DNA accessibility prediction result) to a user, a keyboard, and a pointing device such as a mouse or a trackball by which the user can provide input to apparatus 1700.

Any or all of the systems and apparatus discussed herein, including training engine 210 and prediction engine 220 may be performed by, and/or incorporated in, an apparatus such as apparatus 1700.

One skilled in the art will recognize that an implementation of an actual computer or computer system may have other structures and may contain other components as well, and that FIG. 17 is a high-level representation of some of the components of such a computer for illustrative purposes.

The foregoing specification is to be understood as being in every respect illustrative and exemplary, but not restrictive, and the scope of the invention disclosed herein is not to be determined from the specification, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

We claim:

1. A method for predicting DNA accessibility in a genomic sample, comprising:
   generating, by a training engine, paired data files from genomic sample data, wherein the genomic sample data pertain to a plurality of cell types;
   configuring a neural network to be trained to predict DNA accessibility based on RNA-seq based gene expression levels, wherein configuring the neural network comprises configuring:
      convolutional layers of the neural network to process a first input comprising DNA sequence data from one of the paired data files to generate a convolved output, and
      at least two fully connected layers of the neural network following the convolutional layers to concatenate the convolved output with a second input comprising the RNA-seq based gene expression levels derived from the one of the paired data files and process the concatenation to generate a DNA accessibility prediction output; and
   training the neural network using the paired data files.

2. The method of claim 1, wherein the genomic sample data include DNase-seq data files and RNA-seq data files.

3. The method of claim 2, wherein the RNA-seq data files include data files having one or more of RNA-seq, polyA mRNA, polyA depleted, and single cell labels.

4. The method of claim 2, further comprising removing RNA-seq data files that include error audit flags from the genomic sample data.

5. The method of claim 1, wherein generating the paired data files from the genomic sample data comprises assigning DNase-seq data files to RNA-seq data files that are at least within a same biotype.

6. The method of claim 5, wherein generating the paired data files comprises assigning the DNase-seq data files to the RNA-seq data files based on matching biosample accessions.

7. The method of claim 5, wherein generating the paired data files comprises assigning the DNase-seq data files to the RNA-seq data files based on being from at least one of a same tissue sample, same cell line, or same patient.

8. The method of claim 5, wherein generating the paired data files comprises randomly assigning a DNase-seq data file to one of a plurality of RNA-seq data files determined to be within a same biotype.

9. The method of claim 1, wherein each of the convolutional layers of the neural network is succeeded by a max-pooling layer.

10. The method of claim 1, wherein training the neural network comprises increasing a dynamic decay rate over a course of training.

11. The method of claim 1, wherein training the neural network comprises using an adaptive moment estimation (Adam) optimization algorithm to optimize one or more network parameters of the neural network.

12. The method of claim 1, wherein the neural network comprises a deep convolutional neural network.

13. The method of claim 1, wherein the neural network comprises a densely connected convolutional neural network.

14. The method of claim 1, wherein the first input comprises a 600-base pair segment of DNA.

15. The method of claim 1, wherein the RNA-seq based gene expression levels correspond to a selected subset of genes.

16. The method of claim 1, wherein the DNA accessibility prediction output is a single prediction.

17. The method of claim 1, further comprising:
configuring a computing device to use the trained neural network to predict DNA accessibility in a genomic sample input comprising RNA-seq data and whole genome sequencing for a new cell type with respect to the genomic sample data.

18. The method of claim 17, wherein the genomic sample input is associated with a cancer cohort.

19. The method of claim 17, wherein the genomic sample input is associated with a tumor.

20. A system for predicting DNA accessibility in a genomic sample, comprising:
a processor;
a main memory device;
a persistent storage device;
a training engine executable on the processor according to software instructions stored in one of the main memory device and the persistent storage device and configured to:
generate paired data files from the genomic sample data, wherein the genomic sample data pertain to a plurality of cell types;
configure a neural network to be trained to predict DNA accessibility based on RNA-seq based gene expression levels, wherein configuring the neural network comprises configuring:
convolutional layers of the neural network to process a first input comprising DNA sequence data from one of the paired data files to generate a convolved output, and
at least two fully connected layers of the neural network following the convolutional layers to concatenate the convolved output with a second input comprising the RNA-seq based gene expression levels derived from the one of the paired data files and process the concatenation to generate a DNA accessibility prediction output; and
train the neural network using the paired data files.

21. The system of claim 20, further comprising:
a prediction engine in communication with the training engine and configured to:
obtain a genomic sample input comprising RNA-seq data and whole genome sequencing for a new cell type with respect to the genomic sample data; and
predict DNA accessibility in the genomic sample input using the trained neural network.

22. A computer program product embedded in a non-transitory computer-readable medium comprising instructions executable by a computer processor for predicting DNA accessibility in a genomic sample, which, when executed by a processor, cause the processor to perform one or more steps comprising:
generating paired data files from genomic sample data, wherein the genomic sample data pertain to a plurality of cell types;
configuring a neural network to be trained to predict DNA accessibility based on RNA-seq based gene expression levels, wherein configuring the neural network comprises configuring:
convolutional layers of the neural network to process a first input comprising DNA sequence data from one of the paired data files to generate a convolved output, and
at least two fully connected layers of the neural network following the convolutional layers to concatenate the convolved output with a second input comprising the RNA-seq based gene expression levels derived from the one of the paired data files and process the concatenation to generate a DNA accessibility prediction output; and
training the neural network using the paired data files.

23. The computer program product of claim 22, wherein the non-transitory computer-readable medium comprises further instructions for:
configuring a computing device to use the trained neural network to predict DNA accessibility in a genomic sample input comprising RNA-seq data and whole genome sequencing for a new cell type with respect to the genomic sample data.

24. A convolutional neural network system comprising:
a sequence of neural network layers, wherein the sequence of neural network layers comprises:
a hierarchical structure comprising a plurality of convolutional layers each succeeded by a max-pooling layer, the hierarchical structure configured to receive a first input comprising DNA sequence data from a paired data file and process the first input to generate a convolved output, wherein the paired data file is generated from genomic sample data for a plurality of cell types; and
at least two fully connected layers following the hierarchical structure, the at least two fully connected layers configured to concatenate the convolved output with a second input comprising RNA-seq based gene expression levels derived from the paired data file and process the concatenation to generate a DNA accessibility prediction output.

25. The system of claim 24, wherein the DNA accessibility prediction output is a single prediction.

26. The system of claim 24, wherein the sequence of neural network layers is trained to predict DNA accessibility based on RNA-seq based gene expression levels using a plurality of batches of paired data files.

27. The system of claim 24, wherein a dynamic decay rate for the sequence of neural network layers is configured to be increased over a course of training.

28. The system of claim 24, wherein one or more network parameters of the sequence of neural network layers are configured to be optimized based on an adaptive moment estimation (Adam) optimization algorithm.

29. The system of claim 24, wherein the sequence of neural network layers comprises a deep convolutional neural network.

30. The system of claim 24, wherein the sequence of neural network layers comprises a densely connected convolutional neural network.

31. A method of processing genomic sample data for a plurality of cell types using a convolutional neural network system comprising a sequence of neural network layers, the method comprising:
   processing a first input comprising DNA sequence data from a paired data file using a hierarchical structure comprising a plurality of convolutional layers each succeeded by a max-pooling layer, wherein the hierarchical structure is configured to receive the first input and process the first input to generate a convolved output, and wherein the paired data file is generated from genomic sample data for a plurality of cell types; and
   processing at least two fully connected layers following the hierarchical structure, wherein the at least two fully connected layers are configured to concatenate the convolved output with a second input comprising RNA-seq based gene expression levels derived from the paired data file and process the concatenation to generate a DNA accessibility prediction output.

32. A computer program product embedded in a non-transitory computer-readable medium comprising instructions executable by a computer processor for processing genomic sample data for a plurality of cell types using a convolutional neural network system, which, when executed by a processor, cause the processor to perform one or more steps comprising:
   processing a first input comprising DNA sequence data from a paired data file using a hierarchical structure comprising a plurality of convolutional layers each succeeded by a max-pooling layer, wherein the hierarchical structure is configured to receive the first input and process the first input to generate a convolved output, and wherein the paired data file is generated from genomic sample data for a plurality of cell types; and
   processing at least two fully connected layers following the hierarchical structure, wherein the at least two fully connected layers are configured to concatenate the convolved output with a second input comprising RNA-seq based gene expression levels derived from the paired data file and process the concatenation to generate a DNA accessibility prediction output.

* * * * *